United States Patent
Solem et al.

(10) Patent No.: US 11,141,272 B2
(45) Date of Patent: *Oct. 12, 2021

(54) METHODS FOR IMPROVING HEART VALVE FUNCTION

(71) Applicant: Edwards Lifesciences AG, Nyon (CH)

(72) Inventors: Jan Otto Solem, Bjarred (SE); David Alon, Zichron Yaacov (IL)

(*) Notice: Subject to any disclaimer, the term of this patent is extended or adjusted under 35 U.S.C. 154(b) by 339 days.

This patent is subject to a terminal disclaimer.

(21) Appl. No.: 16/280,342

(22) Filed: Feb. 20, 2019

(65) Prior Publication Data
US 2019/0175337 A1 Jun. 13, 2019

Related U.S. Application Data

(63) Continuation of application No. 15/823,445, filed on Nov. 27, 2017, now Pat. No. 10,213,305, which is a
(Continued)

(51) Int. Cl.
*A61F 2/24* (2006.01)
*A61B 17/04* (2006.01)
*A61B 17/00* (2006.01)

(52) U.S. Cl.
CPC .......... *A61F 2/246* (2013.01); *A61B 17/0401* (2013.01); *A61F 2/2466* (2013.01);
(Continued)

(58) Field of Classification Search
CPC .......... A61F 2/24; A61F 2/246; A61F 2/2463; A61F 2/2487; A61F 2/2466;
(Continued)

(56) References Cited

U.S. PATENT DOCUMENTS 3,671,979 A 6/1972 Moulopoulos
3,689,942 A 9/1972 Rapp
(Continued)

FOREIGN PATENT DOCUMENTS

EP 1472996 A1 11/2004
FR 2728457 A1 6/1996
(Continued)

*Primary Examiner* — Diane D Yabut
*Assistant Examiner* — Christina C Lauer
(74) *Attorney, Agent, or Firm* — Guy L. Cumberbatch

(57) ABSTRACT

A method of deploying a blood-flow controlling device is described for treating a native mitral or tricuspid valve. The blood-flow controlling device includes a blood-flow blocking portion that is slidable over an elongate body portion. The blood-flow blocking portion is preferably an elongate structure fillable with blood having a portion adapted for placement between leaflets of the native valve. An anchor is located on a distal end of the elongate body portion for engagement with heart tissue adjacent a heart apex. An anchor delivery catheter is advanced through the native valve and into an adjacent ventricle. The anchor is then expelled from the anchor delivery catheter into ventricular tissue. The blood-flow blocking portion is then slid along the elongate body portion and positioned between the native leaflets. A locking catheter is then slid along the elongate body portion for locking the blood-flow blocking portion to the elongate body portion.

20 Claims, 27 Drawing Sheets

Related U.S. Application Data continuation of application No. 14/595,648, filed on Jan. 13, 2015, now Pat. No. 9,827,101, which is a continuation of application No. 11/750,272, filed on May 17, 2007, now Pat. No. 8,932,348.

(60) Provisional application No. 60/810,085, filed on Jun. 1, 2006, provisional application No. 60/801,446, filed on May 18, 2006.

(52) U.S. Cl.
CPC ............ *A61B 2017/00243* (2013.01); *A61B 2017/0437* (2013.01); *A61B 2017/0445* (2013.01); *A61B 2017/0453* (2013.01); *A61F 2220/0016* (2013.01); *A61F 2230/0093* (2013.01); *A61F 2240/002* (2013.01)

(58) Field of Classification Search
CPC ...... A61B 17/0401; A61B 2017/00243; A61B 2017/0437; A61B 2017/0445
See application file for complete search history.

(56) References Cited

U.S. PATENT DOCUMENTS

| | | |
|---|---|---|
| 3,898,701 A | 8/1975 | La Russa |
| 4,306,319 A | 12/1981 | Kaster |
| 4,407,271 A | 10/1983 | Schiff |
| 5,167,239 A | 12/1992 | Cohen et al. |
| 5,332,402 A | 7/1994 | Teitelbaum |
| 5,397,351 A | 3/1995 | Pavcnik et al. |
| 5,554,184 A | 9/1996 | Machiraju |
| 5,607,465 A | 3/1997 | Camilli |
| 5,735,842 A | 4/1998 | Krueger et al. |
| 5,957,949 A | 9/1999 | Leonhardt et al. |
| 6,050,972 A | 4/2000 | Zadno-Azizi et al. |
| 6,210,432 B1 | 4/2001 | Solem et al. |
| 6,217,567 B1 | 4/2001 | Zadno-Azizi et al. |
| 6,287,334 B1 | 9/2001 | Moll et al. |
| 6,312,464 B1 | 11/2001 | Navia |
| 6,332,893 B1 | 12/2001 | Mortier et al. |
| 6,358,277 B1 | 3/2002 | Duran |
| 6,419,695 B1 | 7/2002 | Gabbay |
| 6,482,228 B1 | 11/2002 | Norred |
| 6,540,782 B1 | 4/2003 | Snyders |
| 6,602,288 B1 | 8/2003 | Cosgrove et al. |
| 6,605,112 B1 | 8/2003 | Moll et al. |
| 6,629,534 B1 | 10/2003 | St. Goar et al. |
| 6,709,456 B2 | 3/2004 | Langberg et al. |
| 6,730,121 B2 | 5/2004 | Ortiz et al. |
| 6,752,813 B2 | 6/2004 | Goldfarb et al. |
| 6,764,510 B2 | 7/2004 | Vidlund et al. |
| 6,767,362 B2 | 7/2004 | Schreck |
| 6,790,231 B2 | 9/2004 | Liddicoat et al. |
| 6,797,002 B2 | 9/2004 | Spence et al. |
| 6,808,483 B1 | 10/2004 | Ortiz et al. |
| 6,869,444 B2 | 3/2005 | Gabbay |
| 6,875,224 B2 | 4/2005 | Grimes |
| 6,994,092 B2 | 2/2006 | van der Burg et al. |
| 7,004,958 B2 | 2/2006 | Adams et al. |
| 7,011,669 B2 | 3/2006 | Kimblad |
| 7,011,682 B2 | 3/2006 | Lashinski et al. |
| 7,018,406 B2 | 3/2006 | Seguin et al. |
| 7,070,616 B2 | 7/2006 | Majercak et al. |
| 7,077,862 B2 | 7/2006 | Vidlund et al. |
| 7,160,322 B2 | 1/2007 | Gabbay |
| 7,175,656 B2 | 2/2007 | Khairkhahan |
| 7,217,287 B2 | 5/2007 | Wilson et al. |
| 7,226,467 B2 | 6/2007 | Lucatero et al. |
| 7,252,682 B2 | 8/2007 | Seguin |
| 7,291,168 B2 | 11/2007 | Macoviak et al. |
| 7,320,665 B2 | 1/2008 | Vijay |
| 7,322,957 B2 | 1/2008 | Kletschka et al. |
| 7,381,220 B2 | 6/2008 | Macoviak et al. |
| 7,404,824 B1 | 7/2008 | Webler et al. |
| 7,559,936 B2 | 7/2009 | Levine |
| 7,678,145 B2 | 3/2010 | Vidlund et al. |
| 7,758,596 B2 | 7/2010 | Oz et al. |
| 7,785,366 B2 | 8/2010 | Maurer et al. |
| 7,815,580 B2 | 10/2010 | Viswanathan |
| 7,854,762 B2 | 12/2010 | Speziali et al. |
| 7,901,454 B2 | 3/2011 | Kapadia et al. |
| 7,927,370 B2 | 4/2011 | Webler et al. |
| 7,942,928 B2 | 5/2011 | Webler et al. |
| 8,007,428 B2 | 8/2011 | Vijay |
| 8,052,751 B2 | 11/2011 | Aklog et al. |
| 8,070,805 B2 | 12/2011 | Vidlund et al. |
| 8,092,525 B2 | 1/2012 | Eliasen et al. |
| 8,133,213 B2 | 3/2012 | Lashinski |
| 8,172,856 B2 | 5/2012 | Eigler et al. |
| 8,216,302 B2 | 7/2012 | Wilson et al. |
| 8,348,963 B2 | 1/2013 | Wilson |
| 8,449,606 B2 | 5/2013 | Eliasen et al. |
| 8,460,370 B2 | 6/2013 | Zakay |
| 8,486,136 B2 | 7/2013 | Maurer et al. |
| 8,579,967 B2 | 11/2013 | Webler et al. |
| 8,758,430 B2 | 6/2014 | Ferrari et al. |
| 8,758,432 B2 | 6/2014 | Solem |
| 8,778,017 B2 | 7/2014 | Eliasen et al. |
| 8,784,482 B2 | 7/2014 | Randert et al. |
| 8,845,717 B2 | 9/2014 | Khairkhahan et al. |
| 8,888,843 B2 | 11/2014 | Khairkhahan et al. |
| 8,888,844 B2 | 11/2014 | Eliasen et al. |
| 8,932,348 B2 | 1/2015 | Solem et al. |
| 8,968,395 B2 | 3/2015 | Hauser et al. |
| 9,161,837 B2 | 10/2015 | Kapadia |
| 9,232,998 B2 | 1/2016 | Wilson et al. |
| 9,232,999 B2 | 1/2016 | Maurer et al. |
| 9,259,317 B2 | 2/2016 | Wilson et al. |
| 9,289,297 B2 | 3/2016 | Wilson et al. |
| 9,474,605 B2 | 10/2016 | Rowe et al. |
| 9,579,199 B2 | 2/2017 | Hauser et al. |
| 9,636,223 B2 | 5/2017 | Khalil et al. |
| 10,213,305 B2 * | 2/2019 | Solem ..................... A61F 2/246 |
| 10,583,009 B2 | 3/2020 | Hauser et al. |
| 2001/0021872 A1 | 9/2001 | Bailey et al. |
| 2002/0128708 A1 | 9/2002 | Northrup et al. |
| 2002/0198594 A1 | 12/2002 | Schreck |
| 2003/0050682 A1 | 3/2003 | Sharkey et al. |
| 2003/0050694 A1 | 3/2003 | Yang et al. |
| 2003/0078654 A1 | 4/2003 | Taylor et al. |
| 2003/0120341 A1 | 6/2003 | Shennib et al. |
| 2003/0187494 A1 | 10/2003 | Loaldi |
| 2004/0019378 A1 | 1/2004 | Hlavka et al. |
| 2004/0024414 A1 | 2/2004 | Downing |
| 2004/0092858 A1 | 5/2004 | Wilson et al. |
| 2004/0098081 A1 | 5/2004 | Landreville et al. |
| 2004/0117032 A1 | 6/2004 | Roth |
| 2004/0167539 A1 | 8/2004 | Kuehn et al. |
| 2004/0193259 A1 | 9/2004 | Gabbay |
| 2004/0225233 A1 | 11/2004 | Frankowski et al. |
| 2004/0243229 A1 | 12/2004 | Vidlund et al. |
| 2004/0267280 A1 | 12/2004 | Nishide et al. |
| 2005/0038508 A1 | 2/2005 | Gabbay |
| 2005/0038509 A1 | 2/2005 | Ashe |
| 2005/0055089 A1 | 3/2005 | Macoviak et al. |
| 2005/0070999 A1 | 3/2005 | Spence |
| 2005/0075719 A1 | 4/2005 | Bergheim |
| 2006/0058871 A1 | 3/2006 | Zakay et al. |
| 2006/0201519 A1 | 9/2006 | Frazier et al. |
| 2006/0241745 A1 | 10/2006 | Solem |
| 2007/0093890 A1 * | 4/2007 | Eliasen ................. A61F 2/246 623/2.11 |
| 2007/0162071 A1 | 7/2007 | Burkett et al. |
| 2007/0198082 A1 | 8/2007 | Kapadia et al. |
| 2007/0219627 A1 | 9/2007 | Chu et al. |
| 2007/0255399 A1 | 11/2007 | Eliasen et al. |
| 2007/0265700 A1 | 11/2007 | Eliasen et al. |
| 2007/0270943 A1 | 11/2007 | Solem et al. |
| 2007/0282429 A1 | 12/2007 | Hauser et al. |
| 2008/0243245 A1 | 10/2008 | Thambar et al. |
| 2009/0048668 A1 | 2/2009 | Wilson et al. |
| 2009/0069885 A1 | 3/2009 | Randert et al. |

(56) References Cited

U.S. PATENT DOCUMENTS

| | | |
|---|---|---|
| 2009/0137968 A1 | 5/2009 | Rottenberg |
| 2010/0022948 A1 | 1/2010 | Wilson et al. |
| 2010/0023117 A1 | 1/2010 | Yoganathan et al. |
| 2010/0198347 A1 | 8/2010 | Zakay et al. |
| 2010/0298929 A1 | 11/2010 | Thornton et al. |
| 2011/0077733 A1 | 3/2011 | Solem |
| 2011/0184512 A1 | 7/2011 | Webler et al. |
| 2011/0224784 A1 | 9/2011 | Quinn |
| 2012/0143320 A1 | 6/2012 | Eliasen et al. |
| 2013/0338763 A1 | 12/2013 | Rowe et al. |
| 2014/0309732 A1 | 10/2014 | Solem |

FOREIGN PATENT DOCUMENTS

| | | |
|---|---|---|
| JP | S4211278 Y1 | 6/1967 |
| WO | 9930647 A1 | 6/1999 |
| WO | 0047139 A1 | 8/2000 |
| WO | 02062236 A1 | 8/2002 |
| WO | 03003949 A2 | 1/2003 |
| WO | 03028558 A2 | 4/2003 |
| WO | 03049619 A2 | 6/2003 |
| WO | 03003949 A3 | 1/2004 |
| WO | 2004012583 A2 | 2/2004 |
| WO | 2004014258 A1 | 2/2004 |
| WO | 2004021893 A1 | 3/2004 |
| WO | 2004030568 A2 | 4/2004 |
| WO | 2004045378 A2 | 6/2004 |
| WO | 2005007036 A1 | 1/2005 |
| WO | 2005027797 A1 | 3/2005 |
| WO | 2005069850 A2 | 8/2005 |
| WO | 2006032051 A2 | 3/2006 |
| WO | 2006049629 A1 | 5/2006 |
| WO | 2006111391 A1 | 10/2006 |
| WO | 2006127509 A2 | 11/2006 |
| WO | 2007050256 A2 | 5/2007 |

* cited by examiner

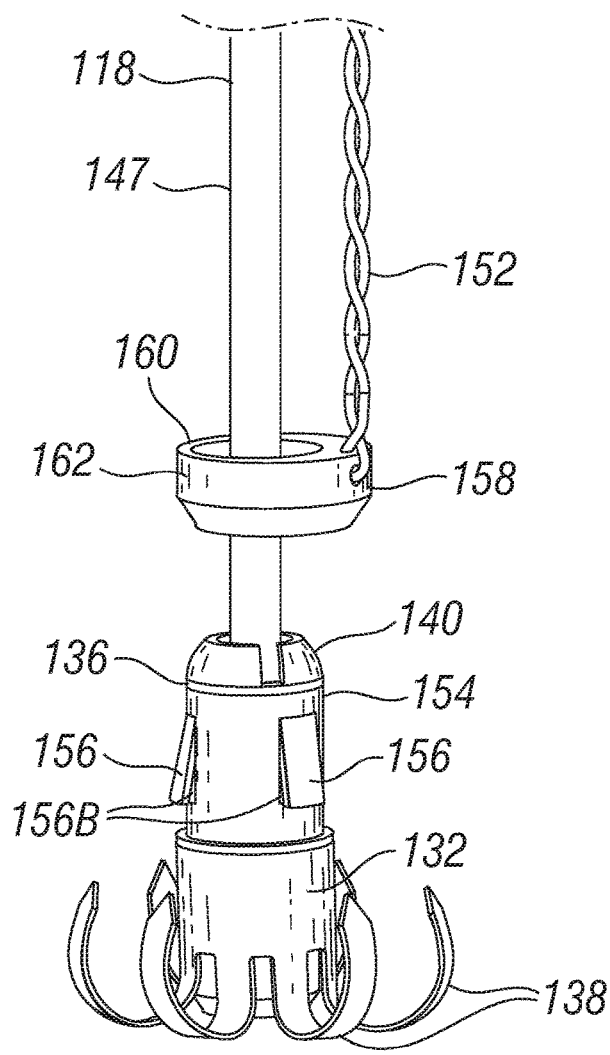
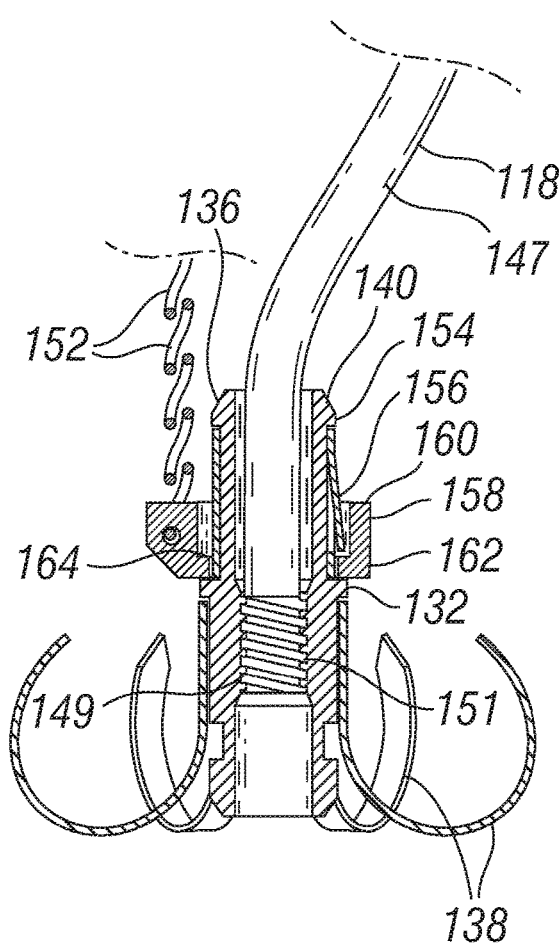
Fig. 12A
Fig. 12B

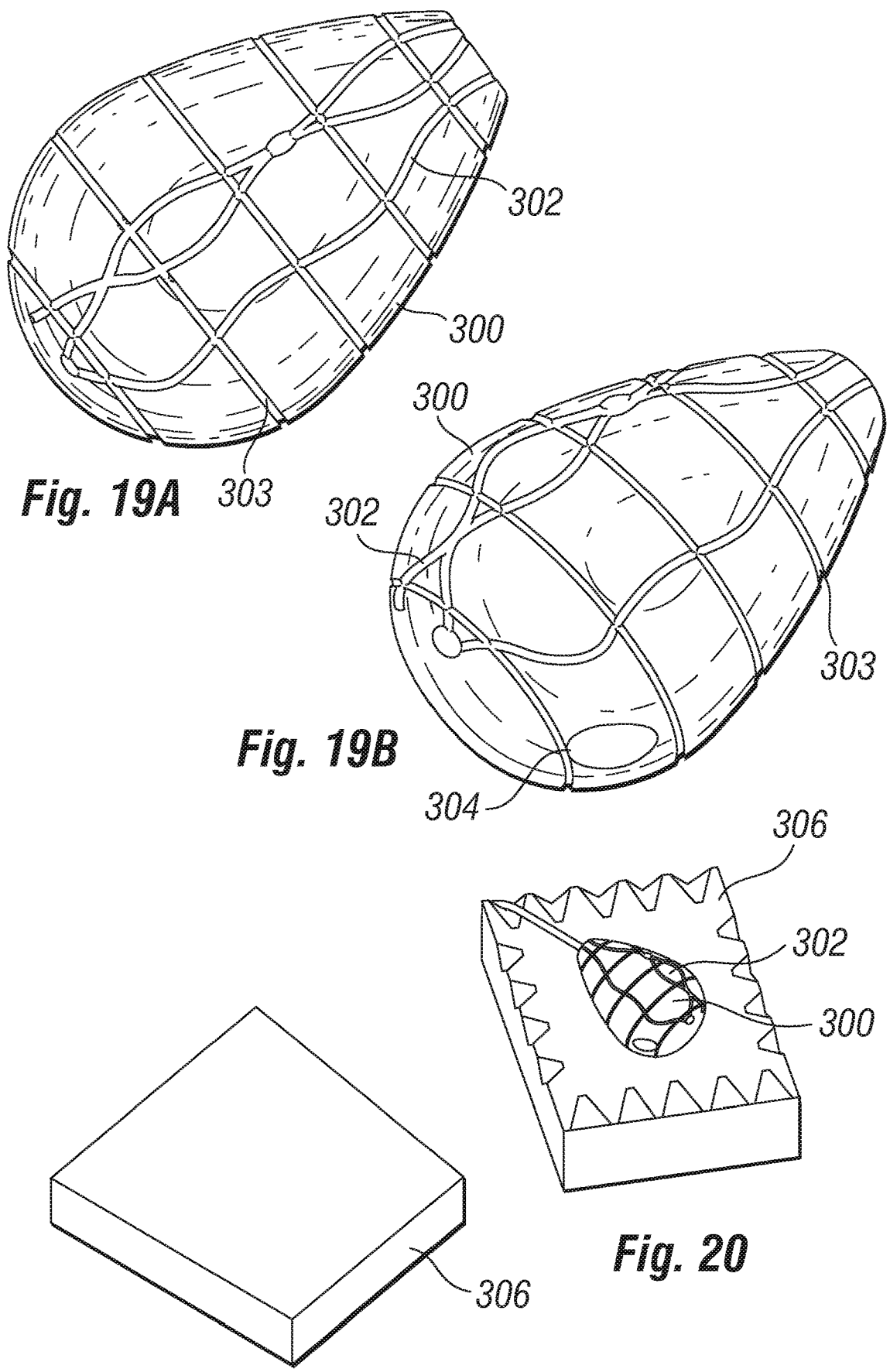

METHODS FOR IMPROVING HEART VALVE FUNCTION

RELATED APPLICATIONS

This application is a continuation of U.S. application Ser. No. 15/823,445, filed Nov. 27, 2017, now U.S. Pat. No. 10,213,305, which is a continuation of U.S. application Ser. No. 14/595,648, filed Jan. 13, 2015, now U.S. Pat. No. 9,827,101, which is a continuation of U.S. application Ser. No. 11/750,272, filed May 17, 2007, now U.S. Pat. No. 8,932,348, which claims the benefit of U.S. Application No. 60/801,446 filed May 18, 2006, and also the benefit of U.S. Application No. 60/810,085, filed Jun. 1, 2006, the entire disclosures all of which are incorporated by reference.

BACKGROUND OF THE INVENTION

The present invention relates generally to devices and methods for improving the function of a defective heart valve. The devices and methods disclosed herein are particularly well adapted for implantation in a patient's heart for reducing regurgitation through a heart valve.

The function of the heart may be seriously impaired if any of the heart valves are not functioning properly. The heart valves may lose their ability to close properly due to e.g. dilation of an annulus around the valve or a leaflet being flaccid causing a prolapsing leaflet. The leaflets may also have shrunk due to disease, e.g. rheumatic disease, and thereby leave a gap in the valve between the leaflets. The inability of the heart valve to close properly can cause a leak backwards (i.e., from the outflow to the inflow side), commonly referred to as regurgitation, through the valve. Heart valve regurgitation may seriously impair the function of the heart since more blood will have to be pumped through the regurgitating valve to maintain adequate circulation. Heart valve regurgitation decreases the efficiency of the heart, reduces blood circulation, and adds stress to the heart. In early stages, heart valve regurgitation leaves a person fatigued or short of breath. If left unchecked, the problem can lead to congestive heart failure, arrhythmias or death.

Regurgitation through the mitral valve, sometimes referred to as mitral insufficiency or incompetence, is a particularly common problem that affects the health of millions of adults. By some estimates, mitral valve regurgitation affects as many as one in five people over age 55. The mitral valve is positioned on the left side of the heart between the left atrium and left ventricle. The mitral valve comprises an annulus, anterior and posterior leaflets, and chordae for attaching the leaflets to papillary muscles. Changes in the geometric configurations of the left ventricle, papillary muscles and mitral annulus may adversely affect the function of the mitral valve and lead to regurgitation. Other factors such as disease, calcification, infection and injury may also cause mitral valve regurgitation.

Heart valve disease, such as mitral valve regurgitation, is typically treated by replacing or repairing the diseased valve during open-heart surgery. However, open-heart surgery is highly invasive and is therefore not an option for many patients. For high-risk patients, a less-invasive method for repair of heart valves is considered generally advantageous. In U.S. Pat. No. 6,210,432 to Solem et al., a less invasive method has been proposed for treating mitral insufficiency without the need for cardiopulmonary by-pass and opening of the chest and heart. The method uses a device comprising an elongate body having such dimensions as to be insertable into the coronary sinus, which is a vein that substantially encircles the mitral orifice and annulus and drains blood from the myocardium to the right atrium. The elongate body has two states, in a first of which the elongate body has a shape that is adaptable to the shape of the coronary sinus, and to the second of which the elongate body applies a compressive force along a posterior region of the mitral valve annulus. The compressive force applied to the mitral valve annulus pushes the mitral valve leaflets into closer proximity and reduces regurgitation. However, due to variations in the type of mitral valve disease and the location of the coronary sinus relative to the mitral valve annulus, this approach may not be suitable for all patients.

In another method, catheter-based procedures have been developed for treating the mitral valve using an "edge-to-edge" approach. In this approach, the free edges of the anterior and posterior mitral valve leaflets are attached along a central region to create a mitral valve having a double orifice. In one method developed by Edwards Lifesciences Corporation of Irvine, USA, an elongate catheter is advanced into the mitral valve for applying suture to the edges of the mitral valve leaflets. A clip is then advanced over the suture to secure the leaflet edges together. Although this "edge-to-edge" approach has shown great promise, similar to the coronary sinus implant, it has been found that this approach may not be suitable for all patients.

U.S. application Ser. No. 11/407,582 to Solem (hereinafter "the '582 Application"), entitled "A Blood Flow Controlling Apparatus," filed on Apr. 19, 2006, now Publication No. 2006/0241745, discloses a variety of devices and methods for treating heart valves using another less-invasive approach. In the '582 Application, the contents of which are hereby incorporated by reference, preferred embodiments of blood flow controlling devices are described which are primarily configured for delivery into the heart via a percutaneous approach. As described in the '582 Application, percutaneous methods of treating heart valves are often desirable, especially for high risk patients, because extracorporeal circulation is not required. However, there are conditions in which percutaneous procedures may not be appropriate. Accordingly, there is a need for new procedures for treating heart valves using minimally-invasive surgical techniques. It is preferable that such minimally-invasive surgical techniques be capable of treating heart valves without requiring extracorporeal circulation.

Accordingly, there is an urgent need for an alternative device and method of use for treating heart valve disease in a minimally invasive procedure that does not require extracorporeal circulation. It is desirable that embodiments of such a device and method be capable of reducing or eliminating regurgitation through a heart valve. It is also desirable that embodiments of such a device and method be well-suited for treating a mitral valve. It is also desirable that such a device be safe, reliable and easy to deliver. It is also desirable that embodiments of such a device and method be applicable for improving heart valve function for a wide variety of heart valve defects. It is also desirable that embodiments of such a device and method be capable of improving valve function without replacing the native valve. The present invention addresses this need.

OBJECTS AND SUMMARY OF THE INVENTION

Various embodiments of the present invention provide improved devices and methods for improving the function of a defective heart valve. Preferred embodiments are configured to be surgically implanted in a heart using a minimally invasive procedure wherein extracorporeal circulation is not required.

In one preferred embodiment, a blood flow controlling device is provided for improving valve function. The blood flow controlling device comprises a valve-blocking portion (such as an expandable valve portion) and an anchor portion. The valve-blocking portion is configured to be disposed between anterior and posterior leaflets of a mitral valve. In an embodiment of a valve-blocking portion, an expandable valve portion expands during ventricular systole to fill and conform to the gap between the mitral valve leaflets, thereby preventing regurgitation. In one variation, the expandable valve portion comprises a canopy or flap portion and a plurality of tethers. In one preferred embodiment, the blood flow controlling device is configured to be delivered into the heart in a two-stage procedure. More specifically, the anchor portion of the device is initially implanted within the heart and the valve portion is then coupled to the anchor portion after the anchor portion has become sufficiently embedded in the muscular wall of the heart.

In another preferred embodiment, a blood flow controlling device comprises an anchor portion and an expandable valve portion configured to be disposed between anterior and posterior leaflets of a mitral valve. In this embodiment, the expandable valve portion is provided with a plurality of apertures or other openings for allowing some blood to flow backward across the expandable portion. This embodiment advantageously reduces the formation of thrombi by eliminating the pooling of blood within the expandable member without substantially reducing the effectiveness of the device.

Preferred embodiments of the present invention include surgical devices and methods of treating heart valves wherein a blood flow controlling device is delivered into the heart through a small incision in the chest, such as, for example, in the sternum or between the ribs. Preferred embodiments of the surgical methods described herein do not require extracorporeal circulation. For example, in one preferred embodiment, a delivery catheter (or similar delivery device) is inserted through an incision in the chest wall and then through the cardiac tissue into a chamber of the patient's beating heart. The delivery catheter allows a blood flow controlling device to be delivered into the heart in a collapsed configuration and then expanded within the heart for treating a defective heart valve. Because the preferred delivery methods do not require extracorporeal circulation, complications are greatly reduced as compared with traditional open-heart surgery.

In another preferred embodiment, devices and methods are provided for facilitating the manufacture of an anchor portion. The devices and methods are configured for manufacturing an anchor portion having a desired three-dimensional geometry. The devices and methods are particularly well-suited for creating an anchor portion that conforms to the shape of a left atrium. In one variation, a disposable jig is used to mold the anchor portion into a particular three-dimensional shape. If desired, the jig can be created to suit the specific geometry of a patient's left atrium. For example, imaging techniques may be used to determine the dimensions of the left atrium before creating the jig. After molding the anchor portion, the jig can be removed, such as, for example, by breaking it into pieces or dissolving, thereby leaving the molded anchor portion. In one preferred variation, the jig is formed of a gypsum material. If desired, a master jig shape can be used to create additional disposable jigs having the same shape.

BRIEF DESCRIPTION OF THE DRAWINGS

FIG. 12A depicts a perspective view of an anchor portion and elongate body portion with connectors according to an embodiment of the invention prior to attachment;

FIG. 12B depicts a perspective view, in cross section, of the anchor portion and elongate body portion with connectors from FIG. 12A in an attached condition;

FIGS. 19A and 19B are perspective views of a master jig used in the manufacture of anchor portions configured for deployment in a left atrium according to an embodiment of the invention;

FIG. 20 is a perspective view of a silicone mold formed using a master jig according to an embodiment of the invention;

DETAILED DESCRIPTION OF THE INVENTION

Figure 1:
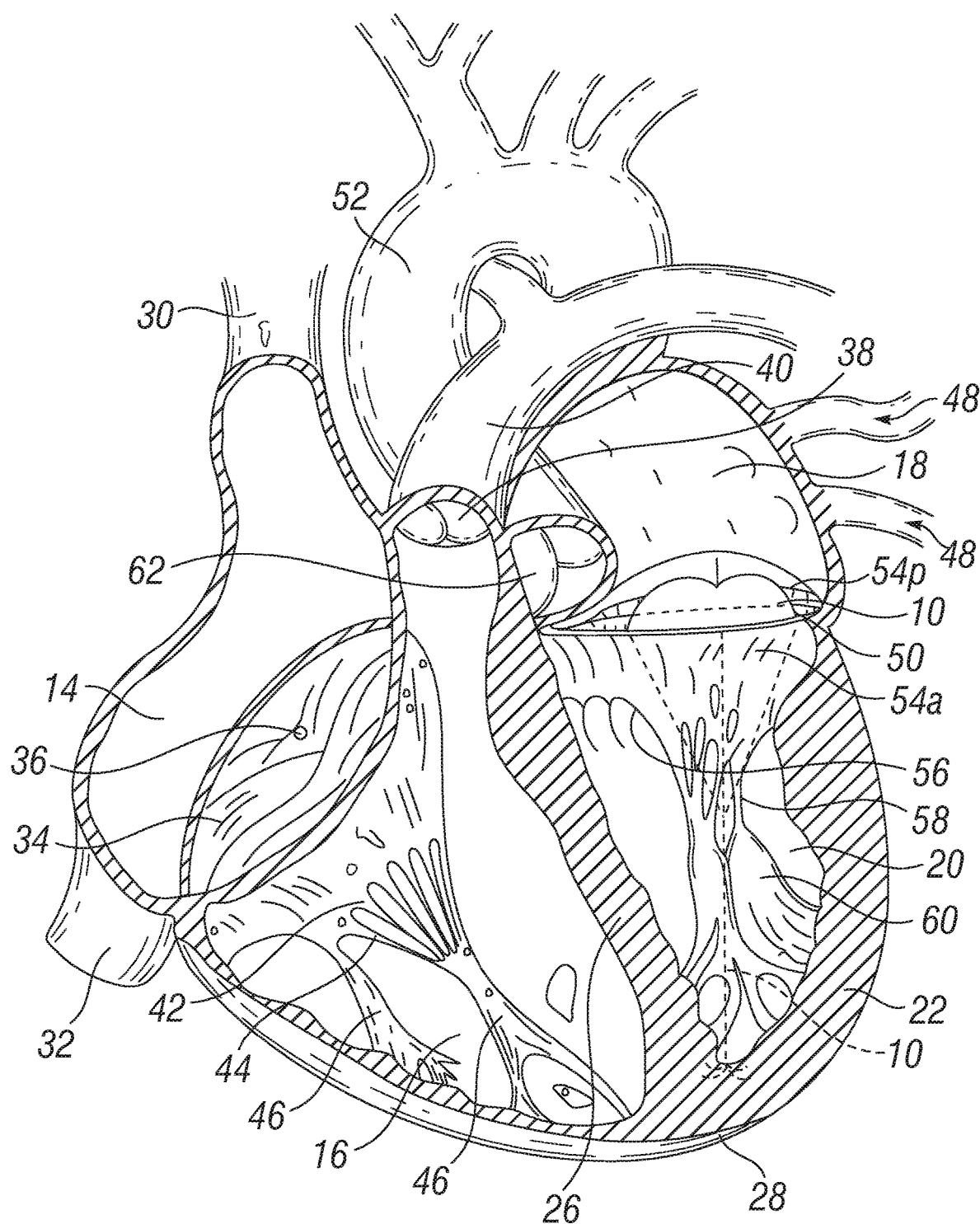
FIG. 1 depicts a side view of a device according to the invention deployed in a human heart, with the heart depicted in cross-section.

With reference to FIG. 1, a device 10 according to the invention is depicted in a heart 12. The heart 12 has four chambers, known as the right atrium 14, right ventricle 16, left atrium 18, and left ventricle 20. In the particular embodiment depicted, the device 10 is deployed in the left ventricle 20.

The general anatomy of the heart 12, which is depicted as viewed from the front of a patient, will be described for background purposes. The heart 12 has a muscular outer wall 22, with an interatrial septum 24 (not visible in FIG. 1, but visible in FIG. 3b, etc.) dividing the right atrium 14 and left atrium 18, and a muscular interventricular septum 26 dividing the right ventricle 16 and left ventricle 20. At the bottom end of the heart 12 is the apex 28.

Blood flows through the superior vena cava 30 and the inferior vena cava 32 into the right atrium 14 of the heart 12. The tricuspid valve 34, which has three leaflets 36, controls blood flow between the right atrium 14 and the right ventricle 16. The tricuspid valve 34 is closed when blood is pumped out from the right ventricle 16 through the pulmonary valve 38 to the pulmonary artery 40 which branches into arteries leading to the lungs (not shown). Thereafter, the tricuspid valve 34 is opened to refill the right ventricle 16 with blood from the right atrium 14. Lower portions and free edges 42 of leaflets 36 of the tricuspid valve 34 are connected via tricuspid chordae tendinae 44 to papillary muscles 46 in the right ventricle 16 for controlling the movements of the tricuspid valve 34.

After exiting the lungs, the newly-oxygenated blood flows through the pulmonary veins 48 and enters the left atrium 18 of the heart 12. The mitral valve 50 controls blood flow between the left atrium 18 and the left ventricle 20. The mitral valve 50 is closed during ventricular systole when blood is ejected from the left ventricle 20 into the aorta 52. Thereafter, the mitral valve 50 is opened to refill the left ventricle 20 with blood from the left atrium 18. The mitral valve 50 has two leaflets (anterior leaflet 54a and posterior leaflet 54p), lower portions and free edges 56 of which are connected via mitral chordae tendinae 58 to papillary muscles 60 in the left ventricle 20 for controlling the movements of the mitral valve 50. Blood from the left ventricle 20 is pumped by power created from the musculature of the heart wall 22 and the muscular interventricular septum 26 through the aortic valve 62 into the aorta 52 which branches into arteries leading to all parts of the body.

Figure 2:
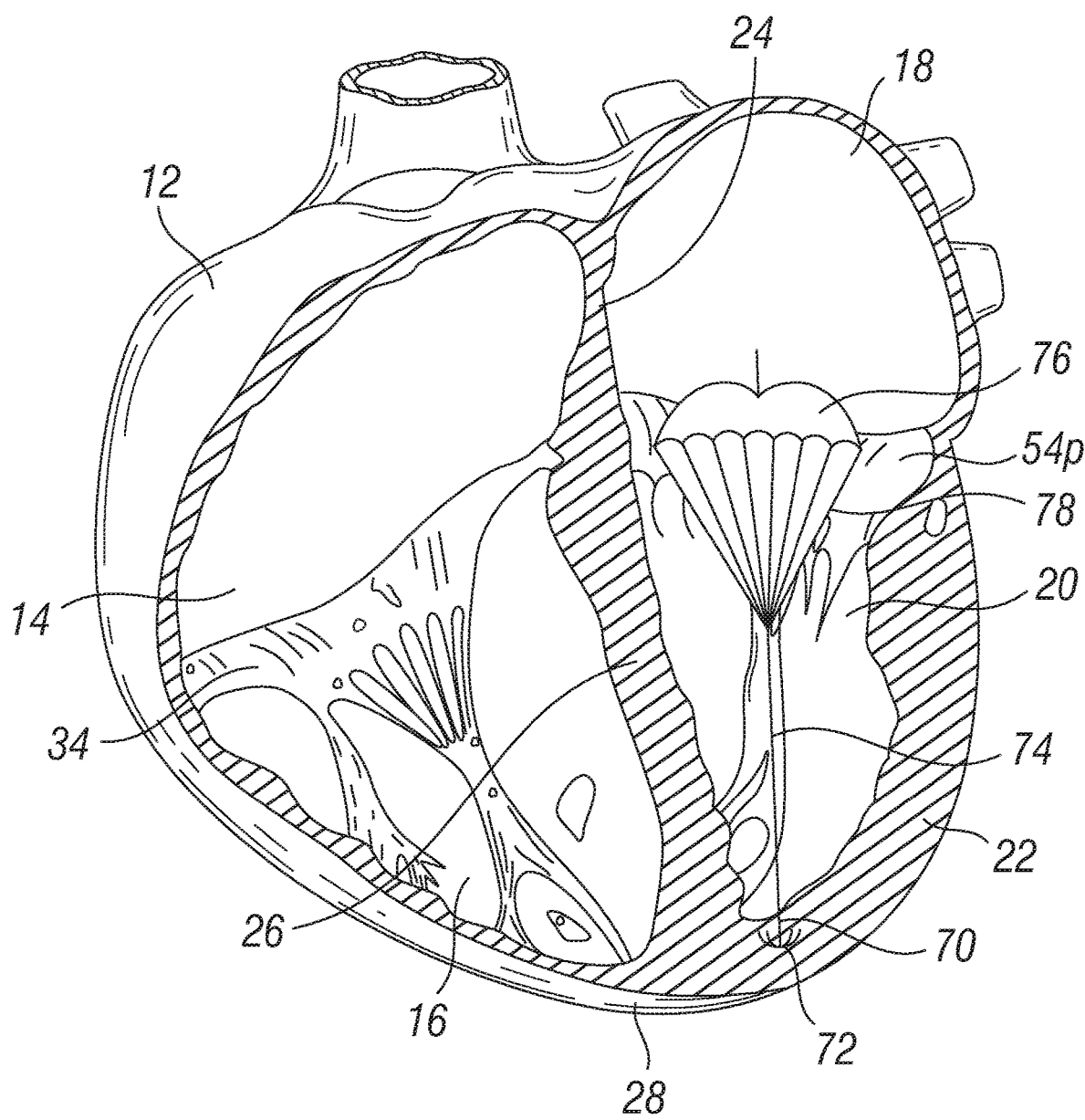
FIG. 2 illustrates a further side view of the heart of FIG. 1, with the heart depicted in a different cross-section and the device deployed therein.

With reference now to FIG. 2, one preferred embodiment of a blood flow controlling device 10 is described and depicted in more detail, with the cutaway view of the heart 12 taken from a position slightly deeper within the heart 12 than in FIG. 1 and thus behind anterior heart structures which had been depicted in FIG. 1 (such as the anterior mitral valve leaflet 54a, etc.) to provide a better view of the device 10. The device 10 can include an anchor portion 70 having one or more anchor members 72, such as screw blades or a plurality of hooks, that embed themselves into the muscular wall 22 of the heart 12. An elongated body portion 74 extends from the anchor portion 70, connecting the anchor portion 70 to the canopy 76 and tethers 78. The elongated body portion 74 can be generally flexible, generally rigid, bendable, formed from a memory material, etc. In the particular embodiment depicted, the elongated body portion 74 is positioned through tile mitral valve 50, and provides a framework for the canopy 76 and the tethers 78. Additional details regarding the construction of a blood flow controlling device 10 for use with the invention can be found in the '582 Application, the contents of which have been specifically incorporated by reference. The canopy 76 of the device 10 thus acts to block the leaking or regurgitating central opening of the mitral valve 50 during ventricular systole. The canopy 76 will generally during inflow through the mitral valve 50, but then inflating in a generally parachute-like fashion during ventricular systole to assist in closing the mitral valve 50.

Figure 3:
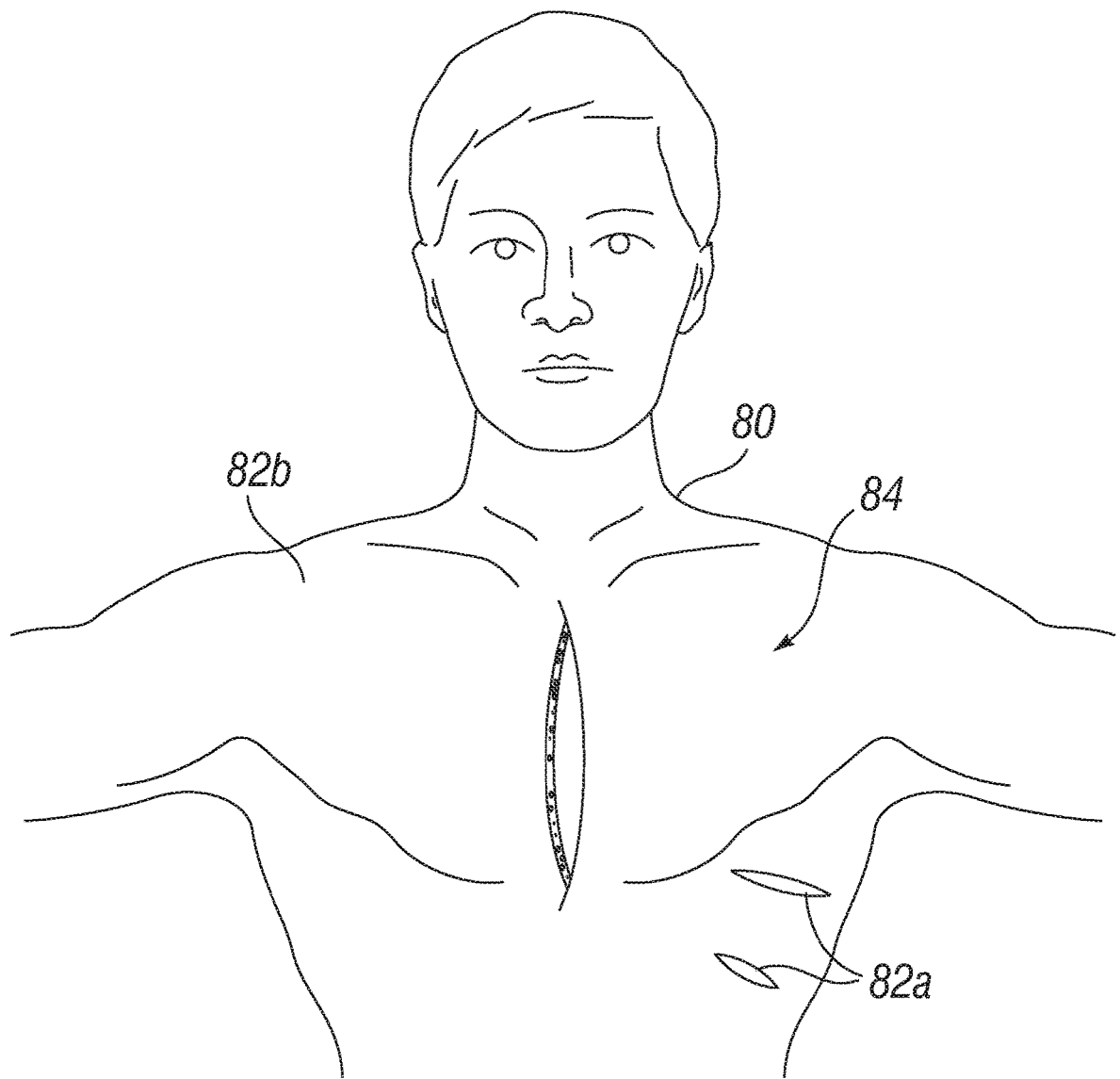
FIG. 3 depicts a front view of a patient with surgical openings through which the device of the invention may be delivered.

With reference to FIG. 3, one preferred method of accessing the heart 12 of a patient 80 for minimally-invasive surgery is illustrated. More particularly, access to the heart 12 is achieved by creating one or more incisions 82a, 82b in the chest wall 84 Incisions can be created between the patient's ribs (as in incisions 82a) or by splitting the patient's sternum (as in incision 82b). In either approach, external surfaces of one or more chambers of the patient's heart may be accessible.

Next, the user selects a desired entry point in the heart through which the delivery catheter is to be inserted. The location of the entry point into the heart will typically depend on the type of blood flow controlling device used (e.g., the devices disclosed the '582 Application) and also on which heart valve (e.g., mitral valve) is targeted for treatment. Examples of various entry points into the heart are described in greater detail below.

Figure 4A:
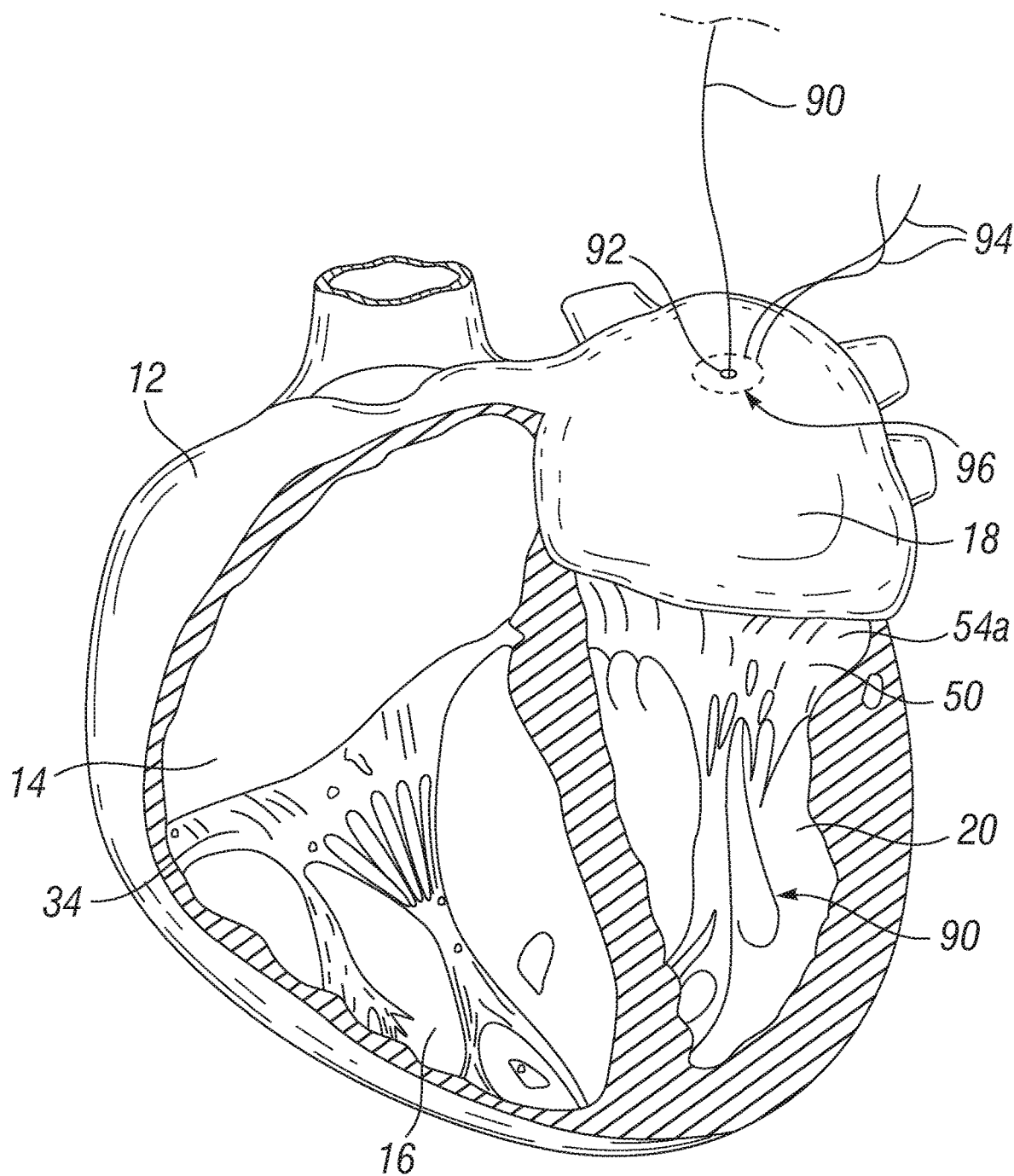
FIG. 4A depicts a front view of a heart, in partial cross section, having a guidewire passing through an entry point in the left atrium and between the leaflets of the mitral valve.

With reference to FIG. 4A, in one preferred delivery method, a guidewire 90 is introduced through an incision 92 in the left atrium 18 and is advanced between the anterior and posterior leaflets 54a, 54p of the mitral valve 50. Since the heart 12 continues to beat during this procedure, steps are preferably taken to minimize blood loss through the incision 92. For example, a purse-string suture 94 can be used in an area 96 around the incision 92 to maintain closure of the incision 92 around the guidewire 90 and thereby minimize blood loss.

Figure 4B:
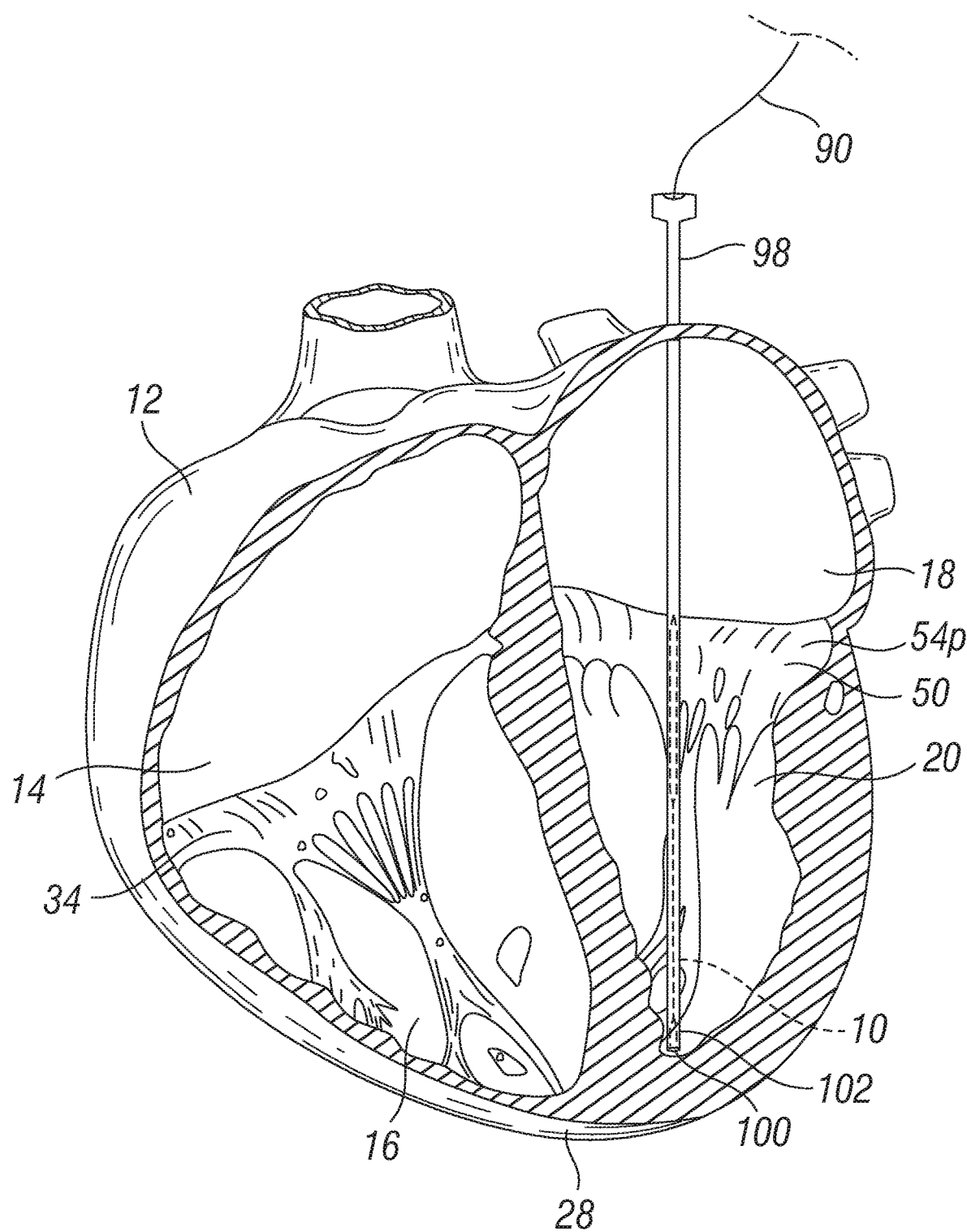
FIG. 4B depicts a front view of a heart, in cross section, with a delivery device that has been advanced into the heart over the guidewire of FIG. 4A.

With reference to FIG. 4B, an elongate delivery catheter 98 is advanced over the guidewire 90 to a desired delivery location 100 within the heart 12. The delivery catheter 98 has the blood flow controlling device 10 secured therewithin. A distal end 102 of the delivery catheter 98 has the anchor 70 secured therewithin, and is positioned within the left ventricle 20. The position of the delivery catheter 98 allows deployment of the anchor 70 into a desired portion of the heart wall 22 in the left ventricle, supporting deployment of the blood flow controlling device 10 for treating valve regurgitation. To ensure that the delivery catheter 98 and blood flow controlling device 10 are properly positioned within the heart 12, contrast dye can be injected in the area, which may be accomplished by injecting the contrast dye through the delivery catheter 98. Alternatively or in addition, other imaging techniques, such as, for example, ultrasound, may be used to determine the position and orientation of the delivery catheter 98 and/or blood flow controlling device 10 within the heart 12. In other alternative procedures, a delivery catheter may be advanced into the heart without the use of a guidewire.

Figure 4C:
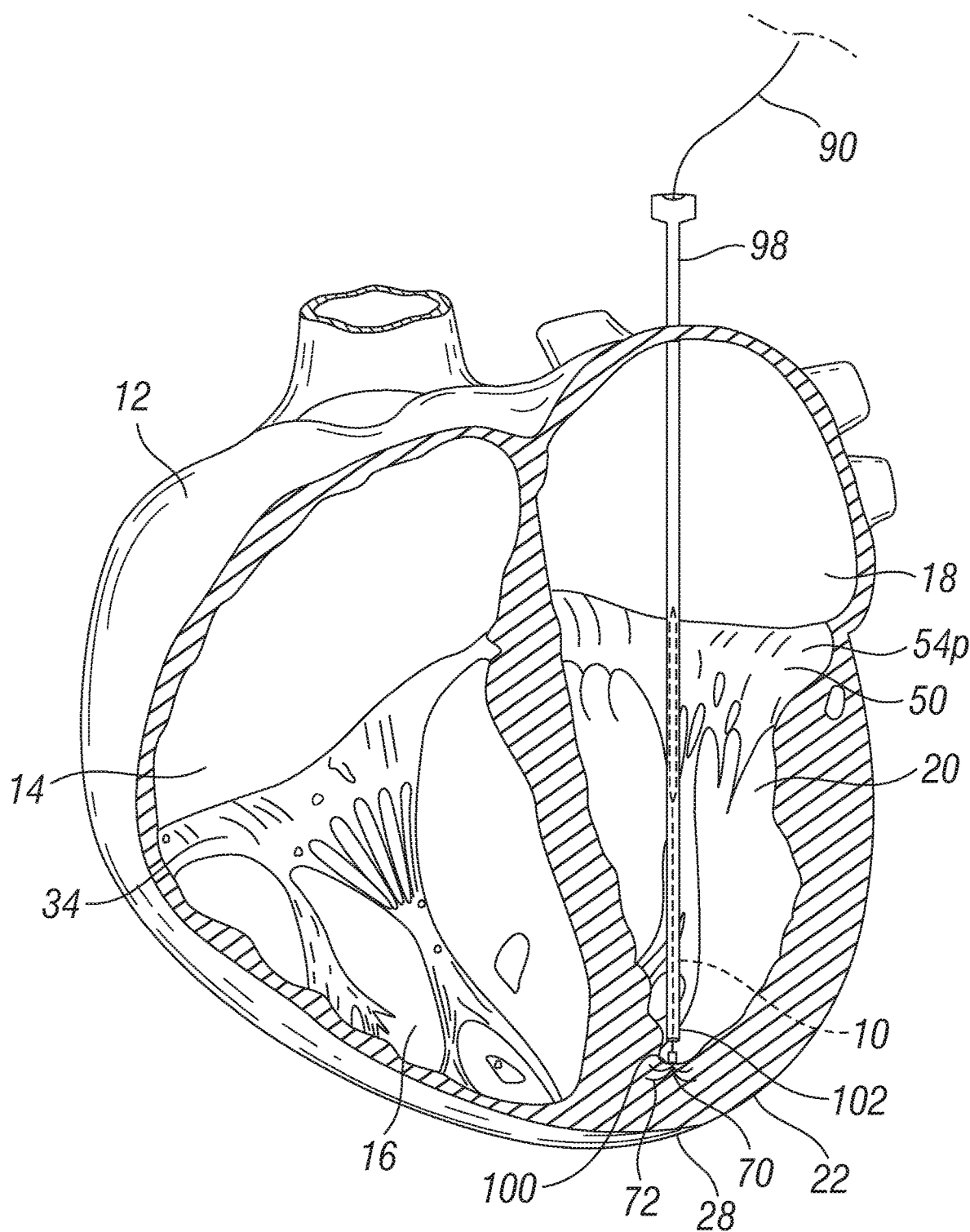
FIG. 4C depicts a front view of a human heart, in cross section, with an anchor portion of a device according to the invention deployed in the heart wall.

In FIG. 4C, the anchor 70 of the device 10 has been extended out of the delivery catheter distal end 102 (which may include retracting the delivery catheter 98 from around the device 10 and/or pushing the device 10 out of the delivery catheter 98). The anchor portion 70 may include anchor members 72 in the form of arms or hooks that expand outward as the anchor portion 70 is exposed, and which are configured to engage and embed into the muscular heart wall and/or other heart tissue, such as the heart wall 22 at or adjacent the heart apex 28. Note that because the heart wall 22 at the apex 28 itself is often relatively thin, but is often thicker in the areas spaced slightly away from the apex 28, it may be desirable to deploy the anchor portion 70 into the heart wall 22 in an area adjacent but slightly spaced away from the apex 28 in order to take advantage of the thicker tissue in which to deploy the anchor portion 70.

Figure 4D:
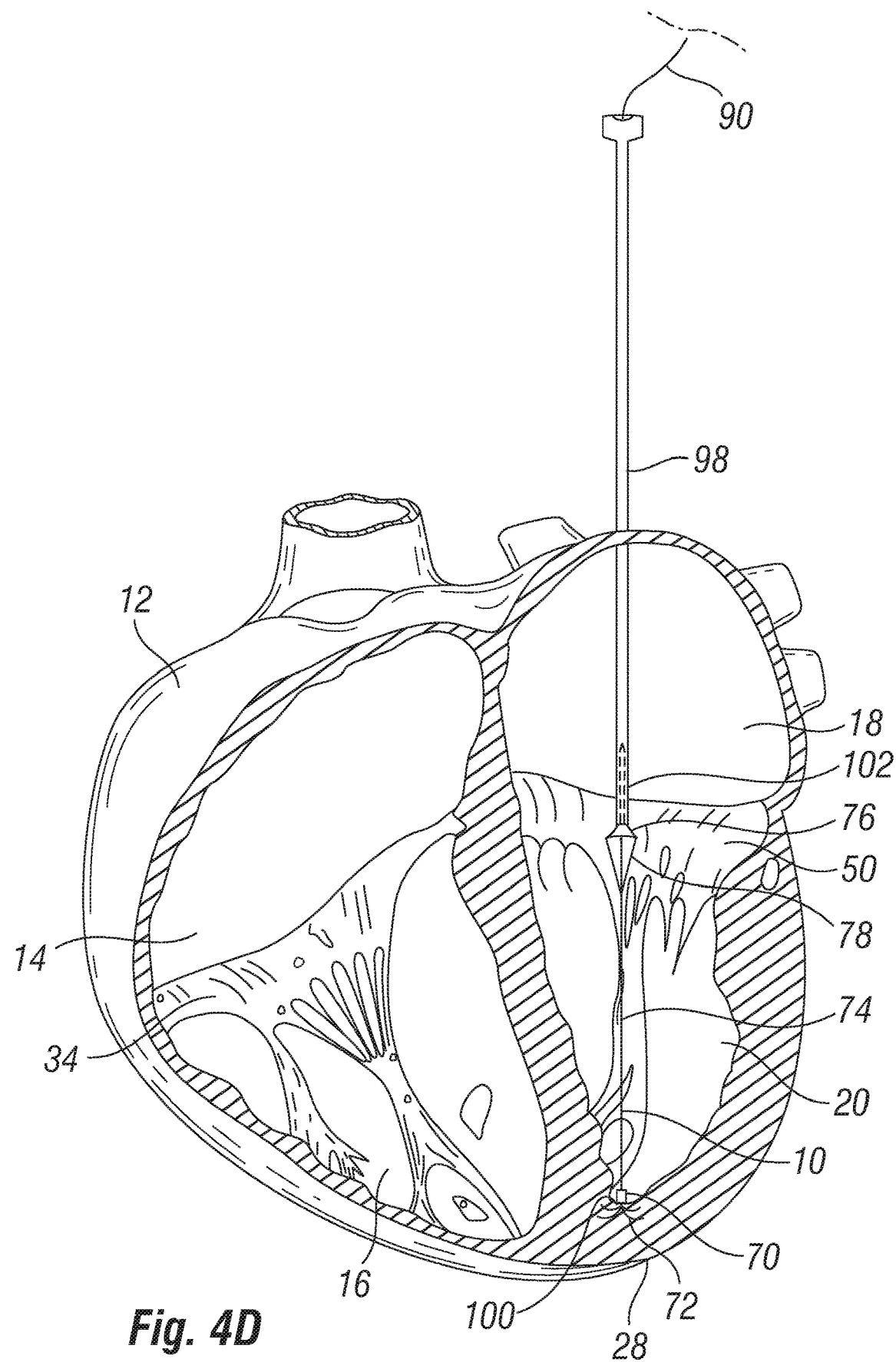
FIG. 4D depicts a front view of a human heart, in cross section, with a device according to the invention partially deployed within the heart.
Figure 4E:
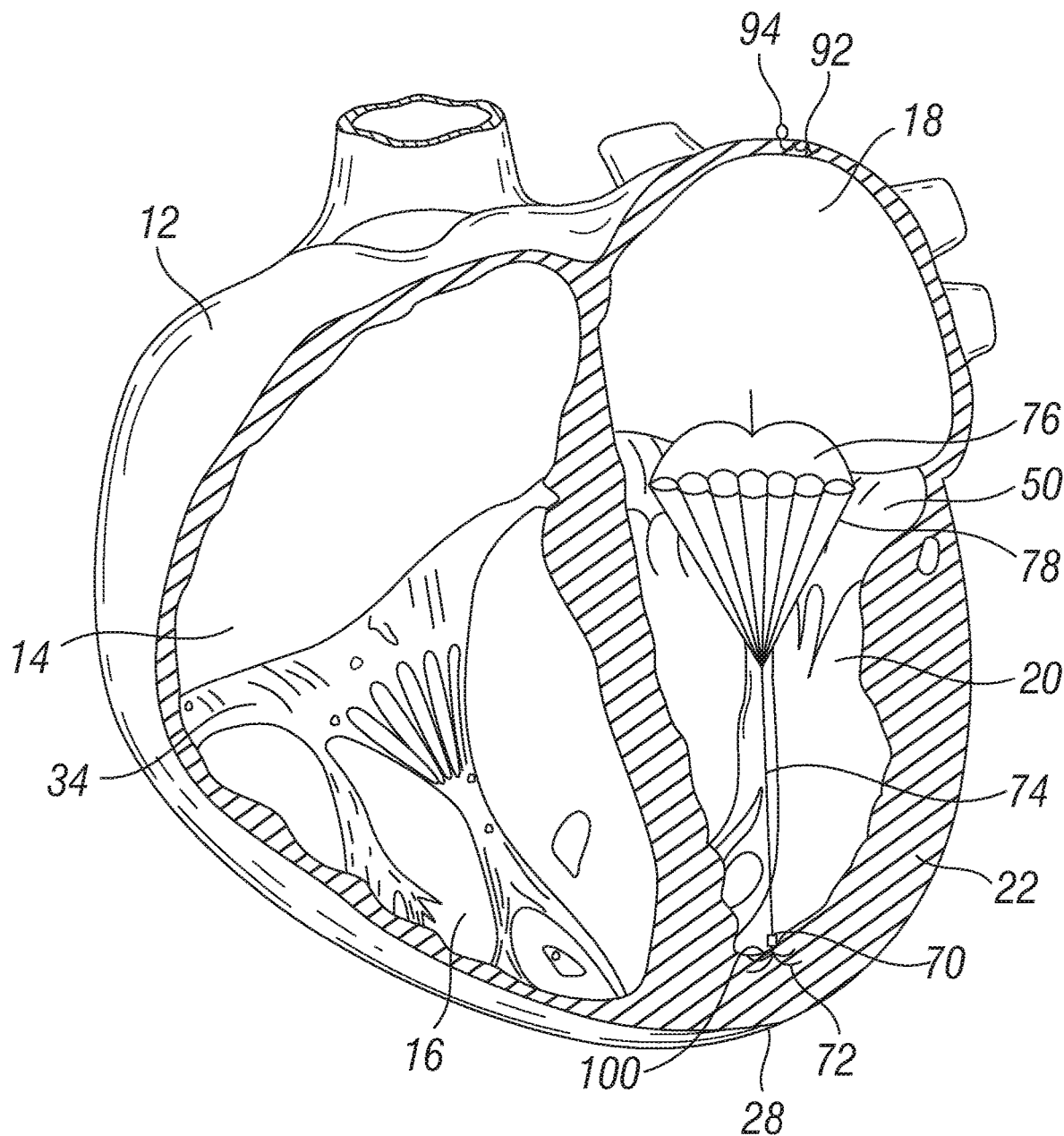
FIG. 4E depicts a front view of a human heart, in cross section, with a device according to the invention fully deployed within the heart.

After the anchor portion 70 is securely deployed in the heart tissue, the delivery catheter 98 can be further retracted, as depicted in FIG. 4D, exposing additional portions of the device 10, including the elongate body portion 74, the connecting tethers 78, and part of the canopy 76. In FIG. 4E, the delivery catheter 98 is completely removed from the device 10. The device 10 is thus deployed, with the canopy 76 expanding against the mitral valve leaflets 54a, 54p or otherwise blocking at least a portion of the mitral valve opening to reduce or prevent backflow of blood through the mitral valve 50. Accordingly, the device 10 is configured to improve the function of the mitral valve 50 by reducing or eliminating regurgitation through the mitral valve 50 without impeding the flow of blood through the heart 12. After the device 10 is positioned and deployed in the desired position within the heart 12, the delivery catheter 98 is withdrawn from the body and the purse string suture 94 is tied such that no bleeding occurs through the incision 92.

Note that the deployment depicted in FIGS. 4A-4E was conducted through the heart wall around the left atrium 18, and involved deploying the device 10 using a single delivery catheter 88 with the device 10 being deployed in one piece. Depending on the particular application, however, other approaches may be used to enter the heart 12, and the device 10 may be deployed as one or more separate pieces (e.g., anchor portion, elongate body portion, tethers, and canopy), with different pieces being deployed independently and in separate stages and then connected together during the deployment process. Some examples of different approaches into the heart are described below and depicted in FIGS. 5, 6, and 7, while an embodiment of an independent deployment procedure is described below and depicted in FIGS. 8A-8D.

Figure 5:
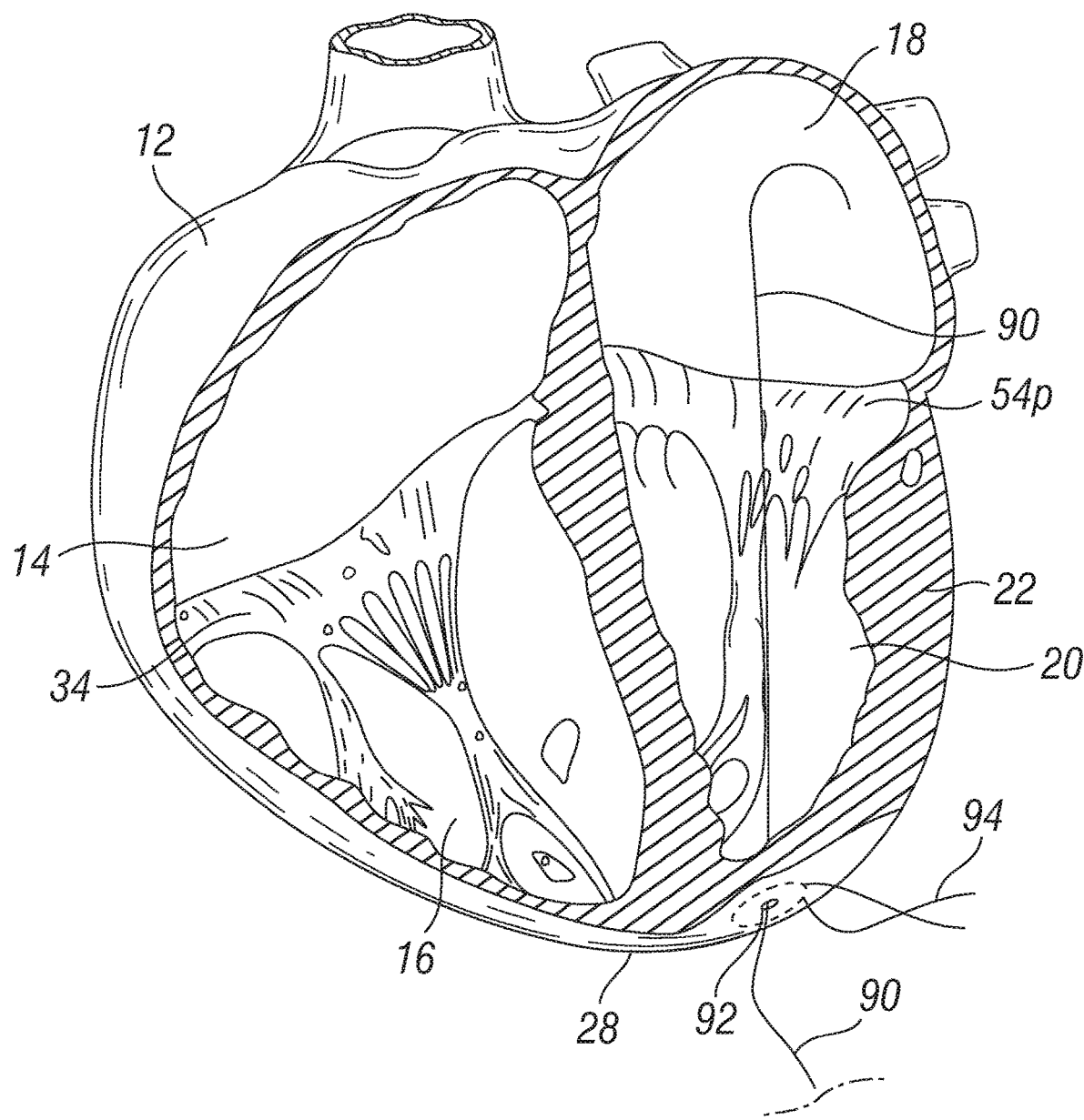
FIG. 5 depicts a front view of a human heat, in cross section, wherein a guidewire is introduced in an alternative delivery method through an entry point in the left ventricle.

It will be appreciated that embodiments of the present invention may be applicable to delivery methods utilizing alternative entry points into the heart 12 With reference to FIG. 5, another preferred entry point is illustrated wherein an incision 92 is created at the base of the heart 12 at or adjacent the apex 28 of the heart 12, and more specifically the apex of the left ventricle 20. As described above, if necessary, a purse string suture 94 may be used to control bleeding and a guidewire 90 may be inserted through the incision 92 and between the mitral valve leaflets 54a (not shown) and 54p for facilitating advancement of a delivery catheter into the heart. A delivery catheter can be advanced through the incision 92 along and/or over the guidewire 90 and between the mitral valve leaflets 54a (not shown) and 54p. By selecting a left ventricle entry point, the user may, for example, more easily deliver a blood flow controlling device that has an anchor portion configured for engagement in the left atrium 18.

Figure 6:
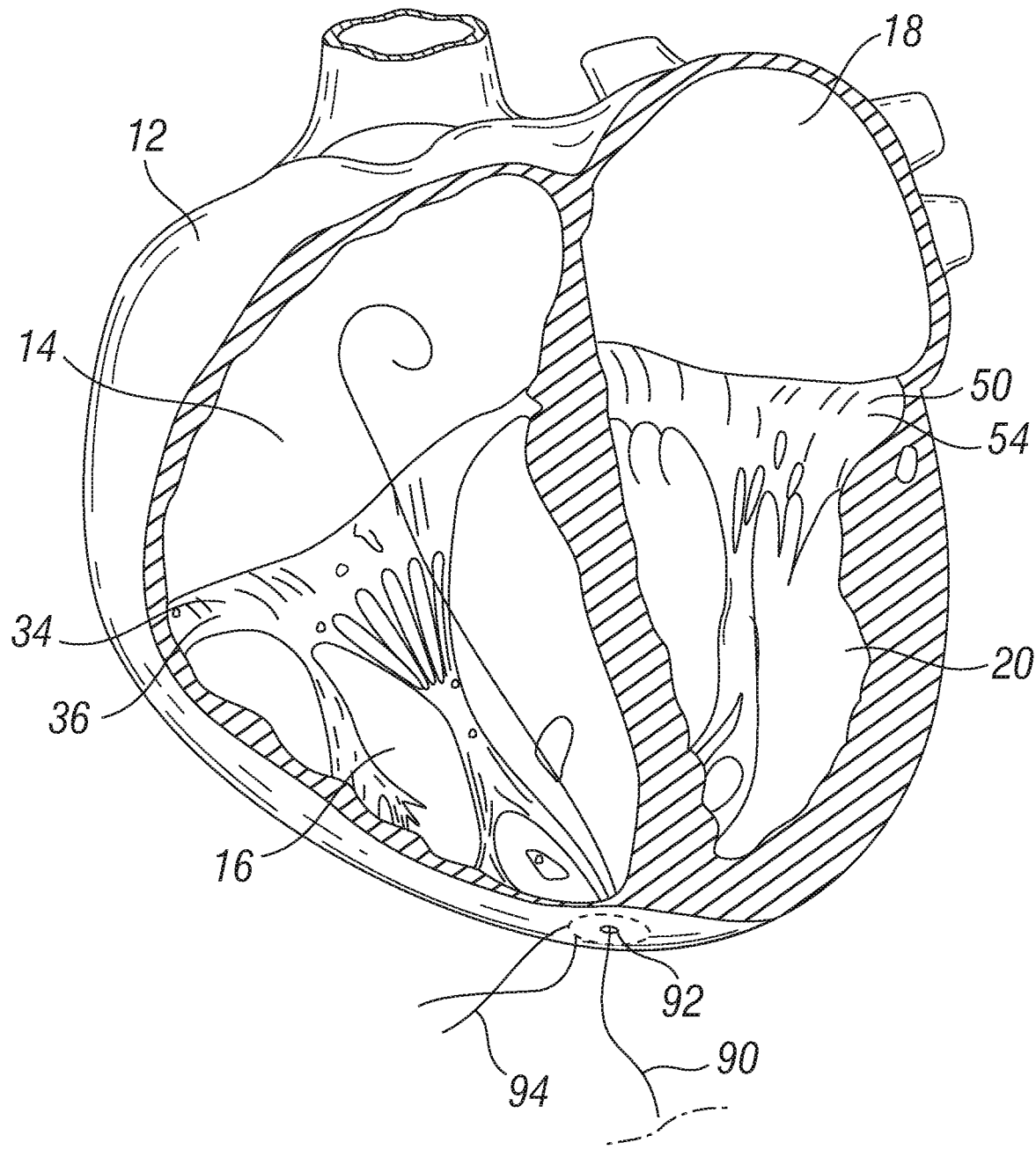
FIG. 6 depicts a front view of a heart, in cross section, wherein another alternative delivery method has a guidewire passing through an entry point in the right ventricle.
Figure 7:
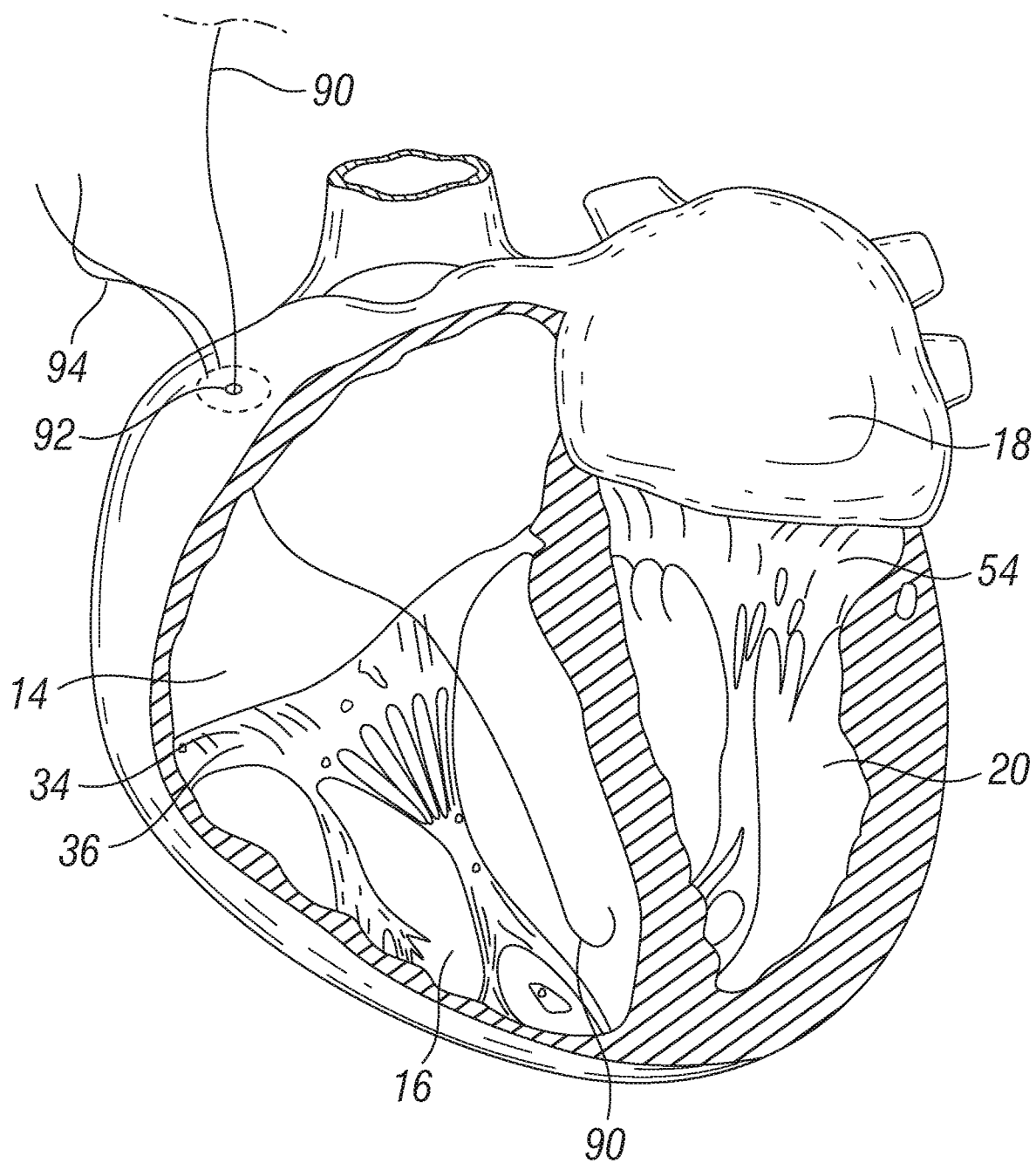
FIG. 7 depicts a front view of a heart, in cross section, wherein another alternative delivery method has a guidewire passing through an entry point in the right atrium.

With reference now to FIG. 6, another entry point is illustrated wherein access into the heart 12 is provided via an incision 92 into the right ventricle 16, with a guide wire 90 advanced between the leaflets 34 of the tricuspid valve 34. This entry point may be used for delivering a blood flow controlling device into the right side of the heart 12 for improving the function of a tricuspid valve 34. Similarly, with reference to FIG. 7, another entry point is illustrated wherein access to the heart 12 is provided via an incision 92 into the right atrium 14. Selection of the entry point will depend on numerous factors, such as, for example, the configuration of the anchor portion (e.g., ventricular or atrial engagement) and the type of valve (e.g., mitral or tricuspid) being treated.

As discussed above, the device 10 may be deployed as a single piece, or may be deployed in two or more separate pieces which are assembled during a multi-stage deployment. While the previously described delivery methods have been generally directed toward a single stage delivery procedure, it should be understood that embodiments of the present invention are well suited for delivery in multiple stages. For example, a delivery procedure may include a first stage in which only an anchor portion of a blood flow controlling device is delivered. A second stage may be performed just after the first stage, or at a later time (e.g., day or weeks later) wherein the valve portion of the device is connected to the anchor portion. The time between the first and second stages may be sufficient to advantageously allow the heart tissue to heal and even grow over the anchor portion, thereby further embedding the anchor portion in the heart. Without the added stress that the valve portion of the device may impart on the tissue, the healing around and over-growth over the anchor may proceed more rapidly with less adverse affects (e.g., unwanted scarring).

FIGS. 8A through 8E depict a two-stage deployment procedure, wherein an anchor portion 70 is deployed in the first stage, and then the remaining structure of the device 10 is advanced to the site and connected to the anchor portion 70 in situ.

Figure 8A:
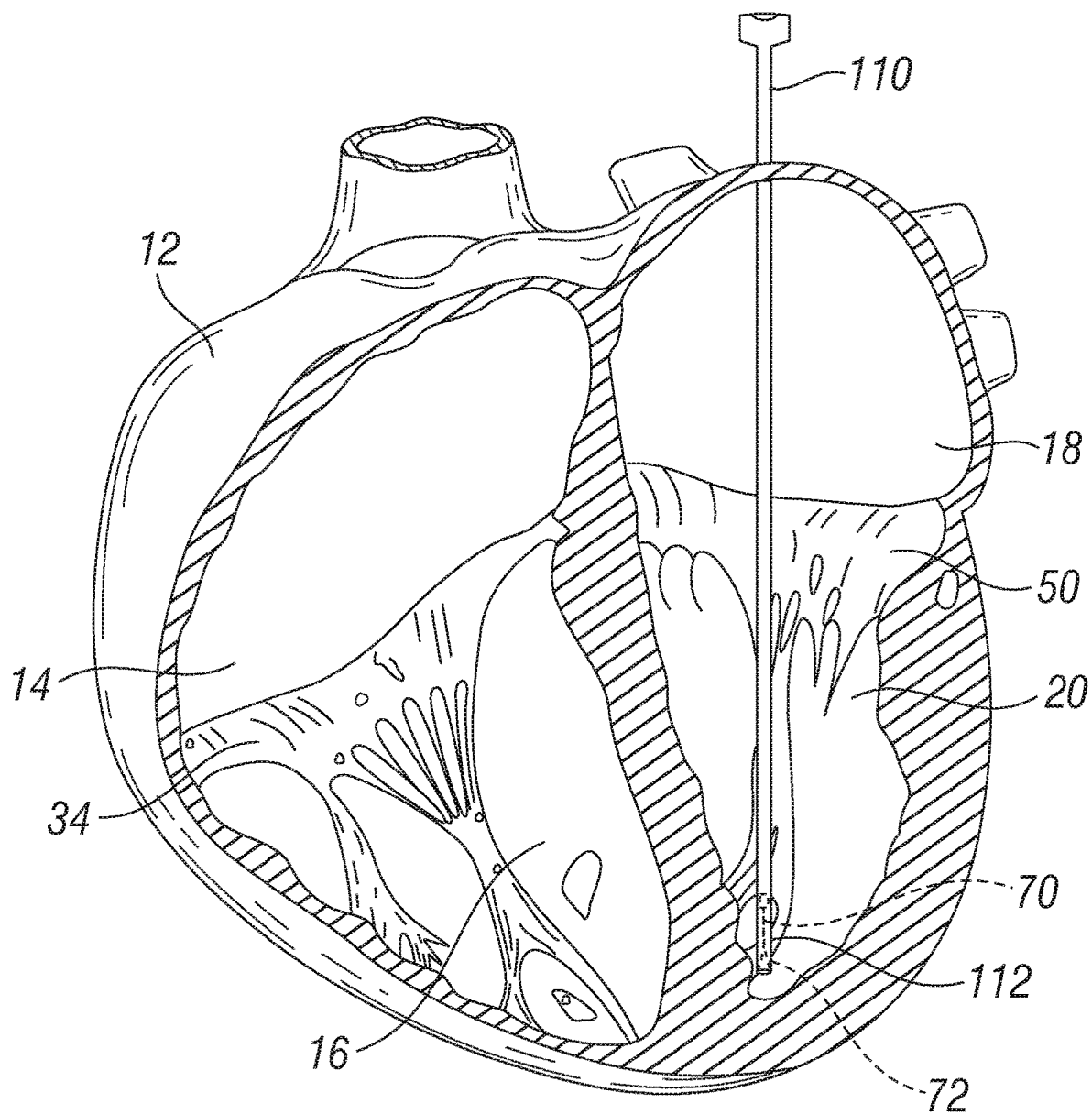
FIG. 8A depicts a front view of a heart, in cross section, wherein an anchor delivery catheter is advanced to deploy a device of the invention within the heart.

In FIG. 8A, an anchor deployment catheter 110 is shown having a distal end 112 advanced to a desired deployment site within the left ventricle 20. The anchor portion 70 is positioned at the anchor deployment catheter distal end 112, and more specifically is contained within the anchor deployment catheter distal end 112. The anchor portion 70 includes multiple anchor members 72 configured to expand outward and embed within the heart tissue when released from the anchor deployment catheter 110, which can be accomplished by pushing the anchor portion 70 out of the anchor deployment catheter 110 and/or withdrawing the anchor deployment catheter 110 from around the anchor portion 70.

Figure 8B:
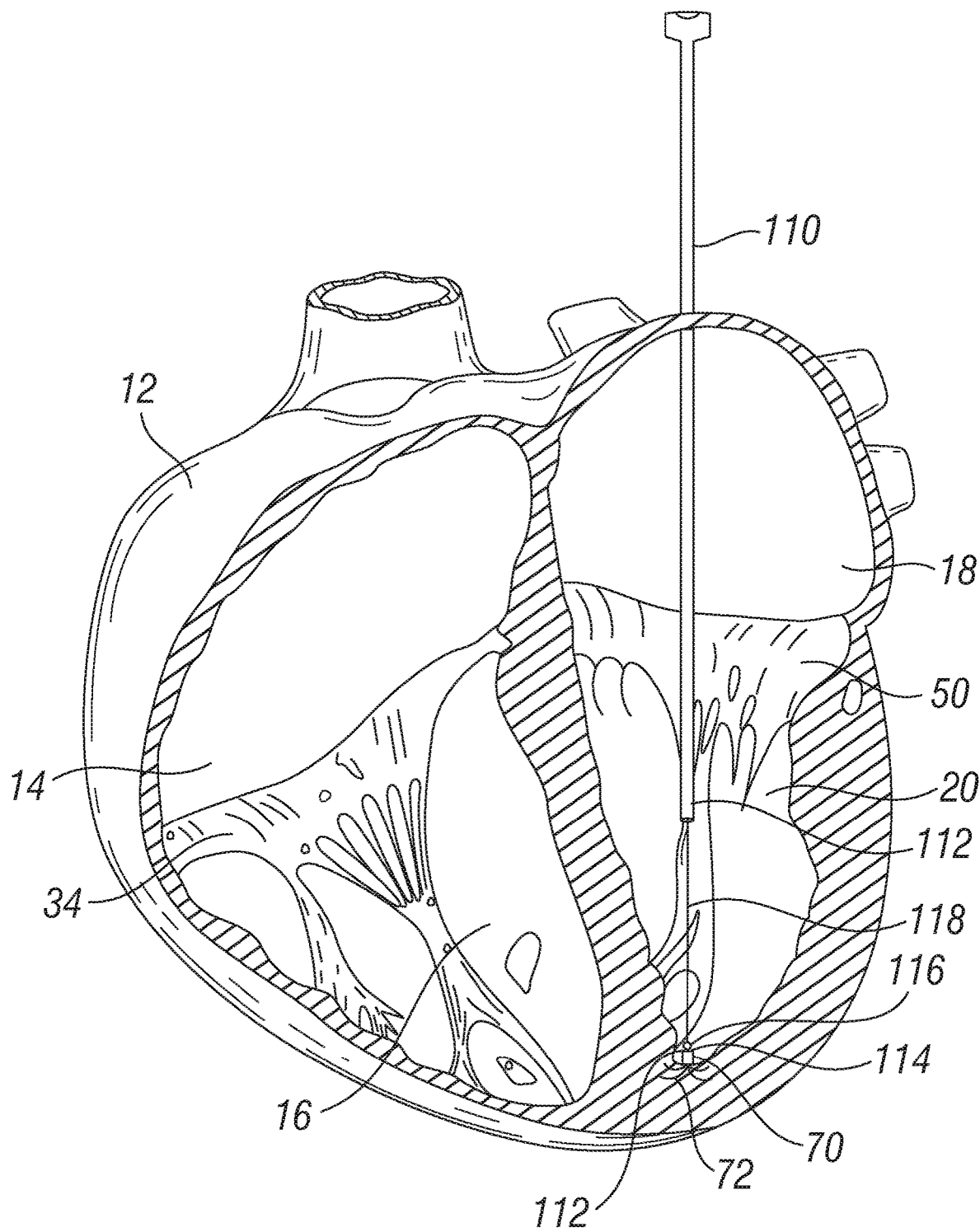
FIG. 8B depicts a front view of the heart of FIG. 8A, in cross section, wherein the anchor delivery catheter is partially withdrawn and an anchor portion according to the invention is deployed within the heart muscle.

In FIG. 8B, the anchor portion 70 has been deployed, with the anchor members 72 embedded into the heart tissue in the lower portion of the left ventricle 20 adjacent the apex 28. The anchor portion 70 has a top portion 112 having an anchor connector 114 configured to receive a mating connector from the rest of the device (i.e., elongate member, canopy, etc.) which will be deployed in the second stage (discussed below). The anchor portion 70 also includes an anchor line opening 116, which is a loop or lumen through which an anchor line 118 can be passed. The particular anchor line 118 depicted in FIG. 8B is a line of suture that passes into the patient and into the heart 12, passes through the anchor line opening 116, and then passes back out of the heart 12 and the patient to form a double suture line. As the anchor deployment catheter 110 is removed from the heart 12, the anchor line 118 is left trailing out of the heart 12 and patient.

Figure 8C:
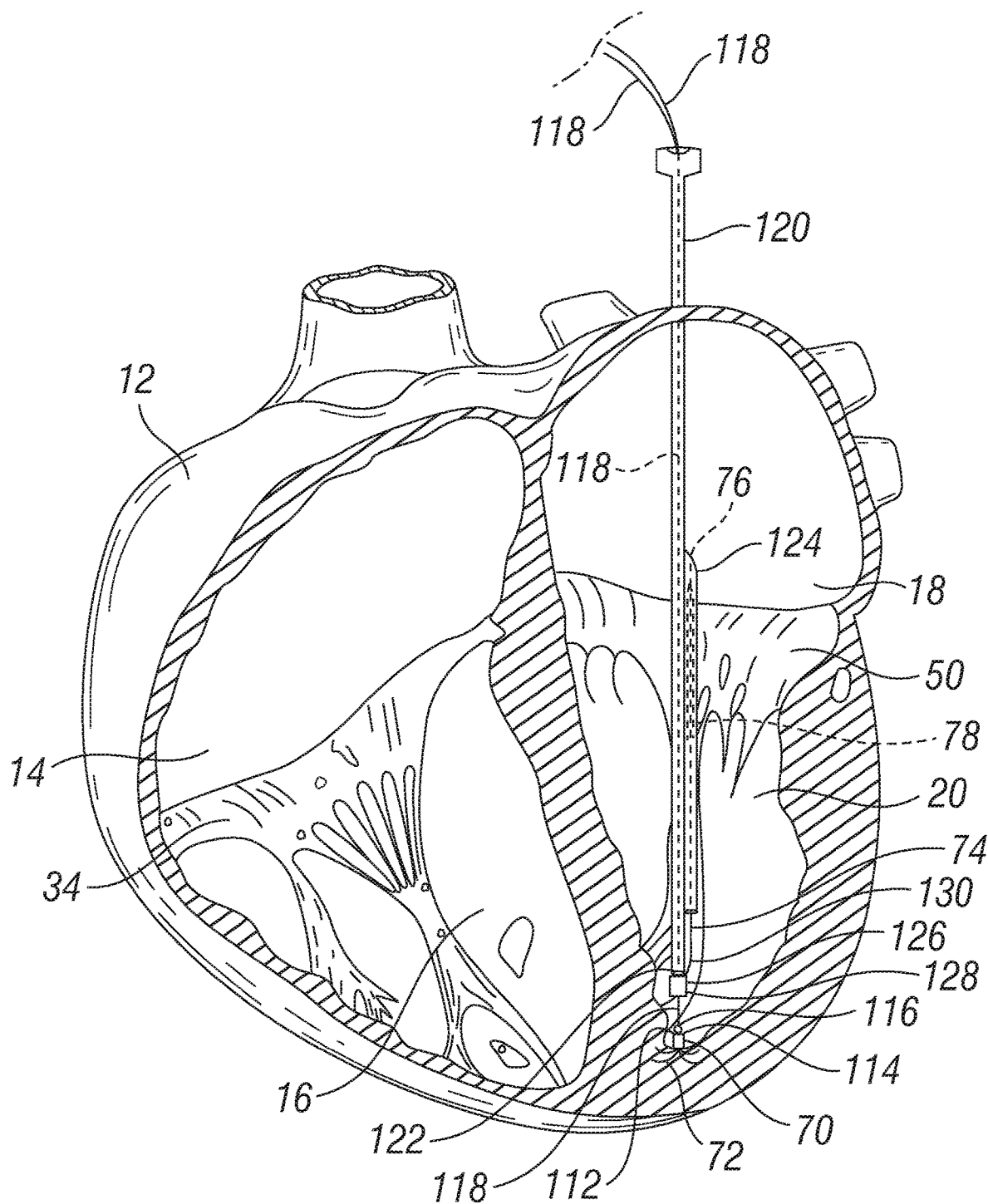
FIG. 8C depicts a front view of the heart of FIG. 8B, in cross section, wherein a second delivery catheter is advanced to deploy a valve blocking portion according to the invention within the heart.

FIG. 8C depicts the second stage of the deployment procedure, wherein the rest of the device is advanced into the heart 12 and secured to the anchor portion 70. A second deployment catheter 120, to which is secured a valve portion 130 (i.e., the combination of the elongate body portion 74, tethers 78, and canopy 76), is advanced to the area in the left ventricle at or adjacent the previously-deployed anchor portion 70. In the particular embodiment depicted, the second deployment catheter 120 is an over-the-wire type catheter having an inner lumen configured to permit the anchor line 118 to slidingly pass therethrough. Note, however, that a so-called rapid-exchange type of delivery catheter could also be used. The second deployment catheter 120 includes a canopy container in the form of a side pocket 124 configured to contain and restrain the canopy 76 during delivery.

As depicted in FIG. 8C, the second deployment catheter 120 is advanced along the anchor line 118 to the anchor portion 70. The elongate body portion 74 includes a distal end 126 having a connector 128 configured to be secured to the anchor portion connector 114. As the second deployment catheter 120 is advanced along the anchor line 118, the elongate body portion distal end 126 and connector 128 will be led into alignment and contact with the anchor portion connector 114. When the elongate body portion connector 128 contacts the anchor portion connector 114, the two connectors 114, 128 are connected together. Note that many different types of connectors are within the scope of the invention, and the particular connectors used with a particular device may be a matter of choice. The connectors may be snap-type or quick-connect connections which automatically connect when the two connectors are brought into contact. The connectors may be manually operated, and/or may include a release device to permit disconnection at a later time.

Figure 8D:
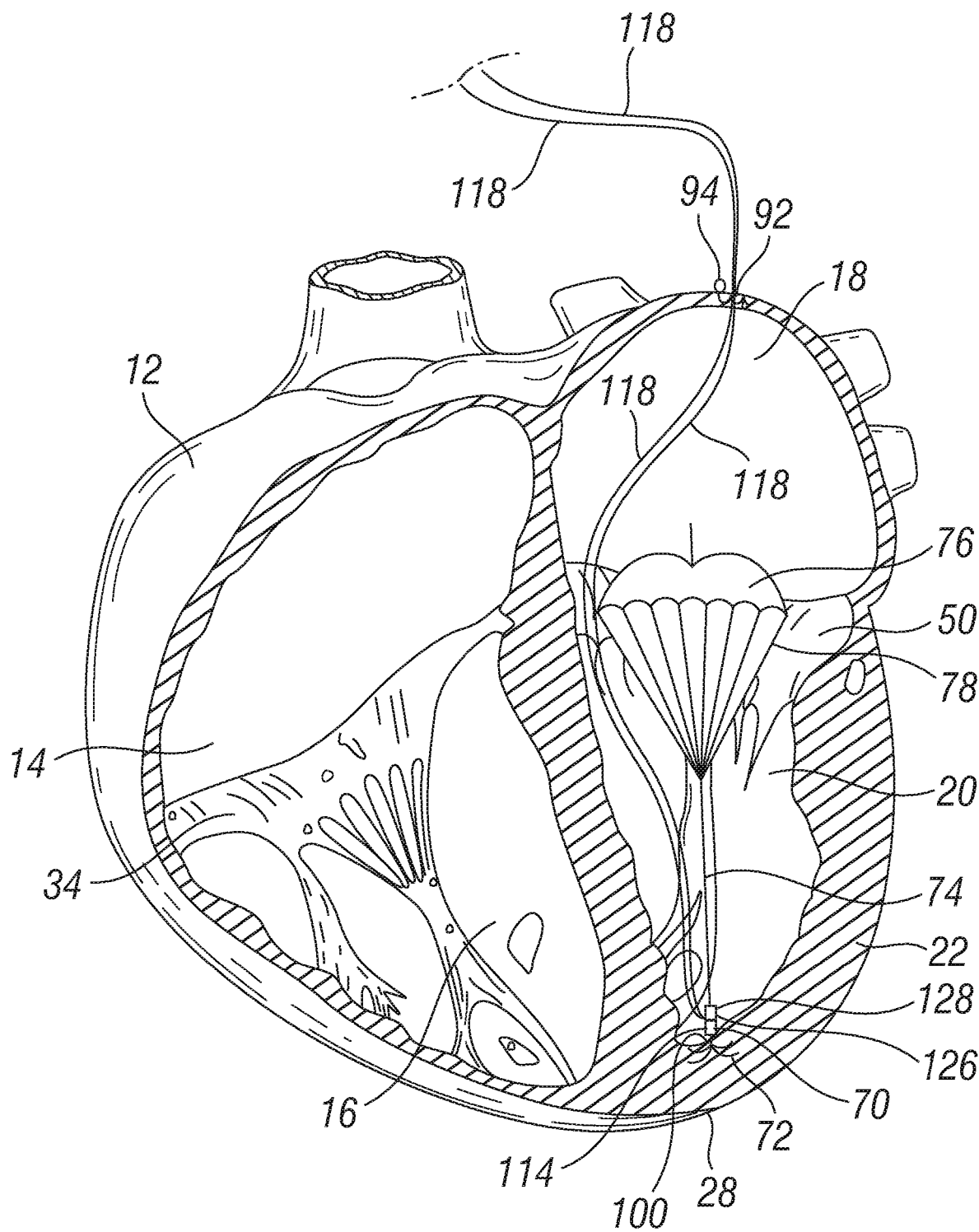
FIG. 8D depicts a front view of the heart of FIG. 8C, in cross section, wherein the device according to the invention is deployed within the heart.

Connection of the two connectors 114, 128 effectively secures the anchor portion 70 to the elongate body portion 74, and thus to the tethers 78 and canopy 76. Once the two connectors 114, 128 are connected, the second deployment catheter 120 can be withdrawn, which will release the canopy 76 from the side pocket to deploy the elongate body member 74, tethers 78, and canopy 76, as depicted in FIG. 8D. In the particular method depicted, the anchor line 118 is still depicted in position passing through the anchor line loop 116 (although the anchor line 118 could have been removed along with, or even prior to, removal of the second deployment catheter 120). The anchor line 118 can now be removed, which in the case of the double suture line depicted can involve releasing one end of the line that passes outside of the heart, and pulling on the other end passing outside the heart. The loose end of the double suture line will thus be pulled into the heart 12 and will be pulled out of the anchor line loop 116, thus releasing the anchor line 118 from the anchor portion 70. With the second deployment catheter 120 and anchor line 118 removed from the patient, the device 10 is fully assembled and deployed.

Note that a two-stage deployment device and method such as that depicted in FIGS. 8A-8D could be useful for situations where a user desires to replace a canopy or other portion of a device. For example, if after the device is entirely deployed in a patient's heart, a user may determine that the expandable valve portion is not of the optimal size or not at an optimal distance from the anchor. Such situations may arise where one or more portions of the patient's heart (e.g., the valve, etc.) has deformed since the initial deployment procedure. In such a situation, a user could remove the initially-deployed expandable valve portion while leaving the anchor portion in place. The user could then attach another expandable valve portion to the anchor portion. Alternatively, the user could simply leave the initial anchor portion in place without attaching another expandable valve portion thereto. The user could also deploy a second expandable valve portion using a second anchor portion.

Figure 9B:
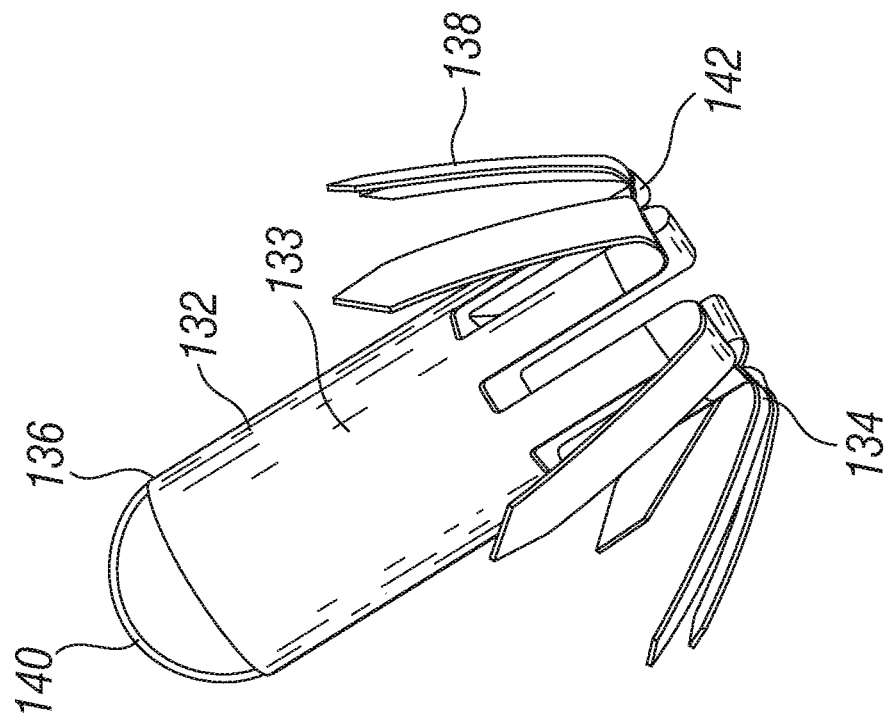
FIGS. 9A and 9B depict side views of an anchor portion according to an embodiment of the invention.
Figure 9A:
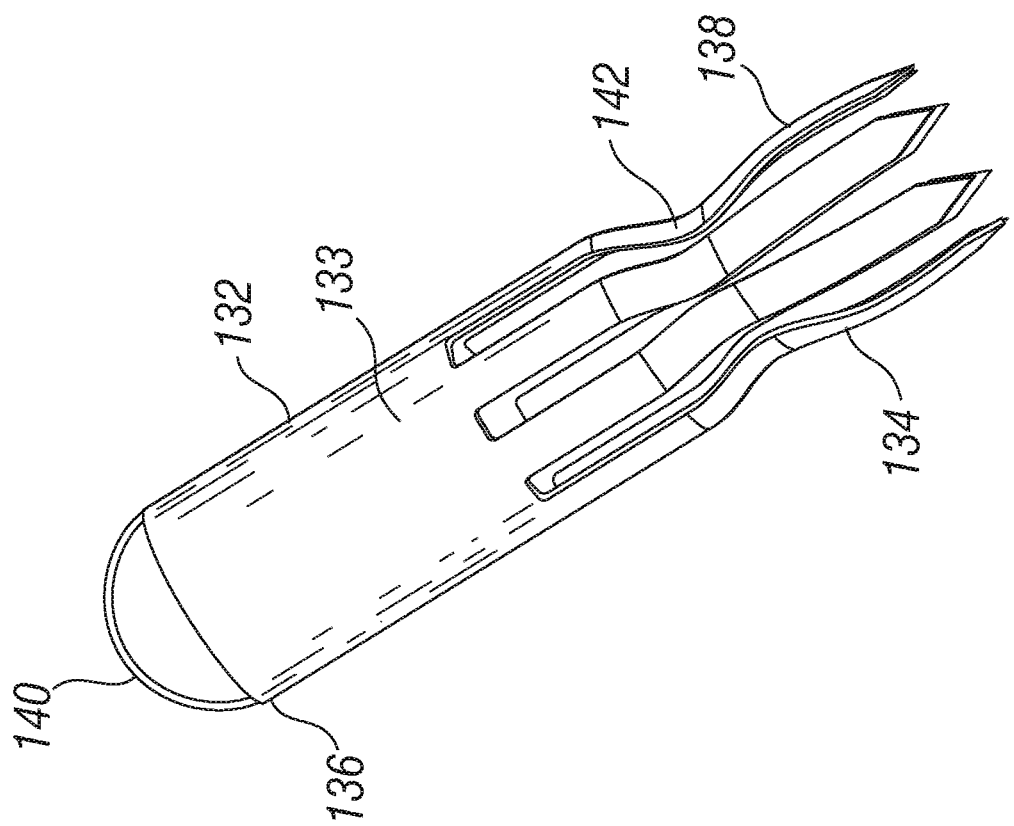

With reference to FIGS. 9A and 9B, for purposes of illustration, another embodiment of an anchor portion 132 is described in more detail. The illustrated anchor portion 132 is particularly well suited for use with a multistage implantation procedure wherein the anchor portion 132 is delivered before a valve portion. The anchor portion 132 comprises a tubular body 133 having a distal end 134 and a proximal end 136, with a plurality of elongated prongs 134 located on the distal end 134 and a coupling member 140 located on the proximal end 136. In the illustrated embodiment, the coupling member 140 takes the form of a loop.

The elongated prongs 138 may be configured to self-expand from the compressed configuration of FIG. 9A to a "flowered" or expanded configuration of FIG. 9B. This expansion may be achieved with a self-curving area 142 that deflects the elongated prongs 138 radially outward from the center of the generally tubular body 133. The prongs 138 may be pointed and/or barbed to facilitate penetration of and engagement with the muscular wall of the heart.

The anchor portion 132 may be formed from various materials and/or combinations thereof. In one embodiment, the anchor portion 132 is formed from a single tube of shape memory material, such as, for example, Nitinol. During manufacture, the shape memory material (or other material forming the anchor portion 132) may be cut using a mechanical or laser cutting tool. After cutting the tube, the expanded or flowered shape can be imparted to the memory of the shape memory material with techniques known in the art (e.g. heat setting the shape).

The surface of the anchor portion 132, including the prongs 138, may be configured to promote tissue growth onto and even into its surface. In one example this growth is achieved by providing a relatively rough and/or porous surface along the anchor portion 132. Additionally, biological coatings of the types known in the art can be included on the surface of the anchor portion 132 to promote healing and tissue growth.

Figures 10A, 10B:
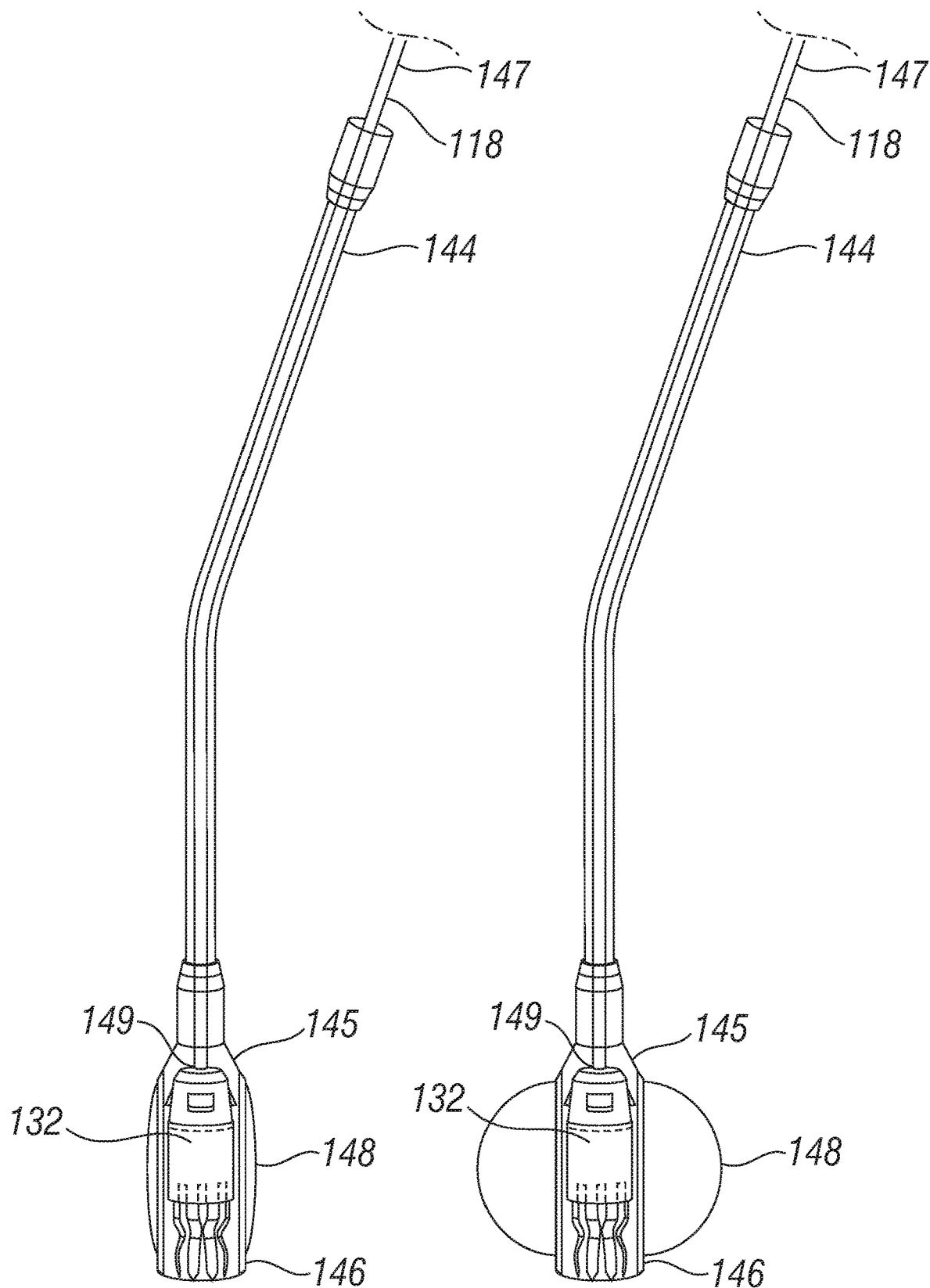
FIGS. 10A-10D illustrate a delivery tool, in partial cross section, for delivering an anchor portion similar to the one depicted in FIGS. 9A and 9B.

With reference to FIGS. 10A through 10D, a method of deploying the anchor portion 132 will be described in more detail. As shown in FIG. 10A, an anchor portion 132 is secured within a distal end portion 145 of an anchor delivery catheter 144. The distal end portion 145 includes a distal end sheath 146 that surrounds the anchor portion 132 and maintains the anchor portion 132 in a compressed configuration during delivery to a treatment site. The anchor delivery catheter 144 also includes an expandable structure such as an expandable balloon 148, which in the embodiment depicted is positioned around a portion of the distal end sheath 146.

Using the illustrated delivery system, the anchor delivery catheter distal end portion 145 containing the anchor portion 132 is advanced through a chest wall and through the cardiac tissue (or through other delivery routes) into a desired heart chamber. When the anchor portion 132 and surrounding distal end sheath 146 are advanced just past the orifice of the valve to be treated (such as a mitral valve as depicted in FIGS. 8A-8D or a tricuspid valve), the expandable balloon 148 can be expanded, as depicted in FIG. 10B. The expandable balloon 148 when expanded can assist in advancement of the anchor delivery catheter distal end portion 145 past the chordae tendinae and other sub-valvular structures by preventing the anchor delivery catheter distal end portion 145 from becoming entangled within or otherwise passing between such structures in an undesired manner.

Figure 10C:
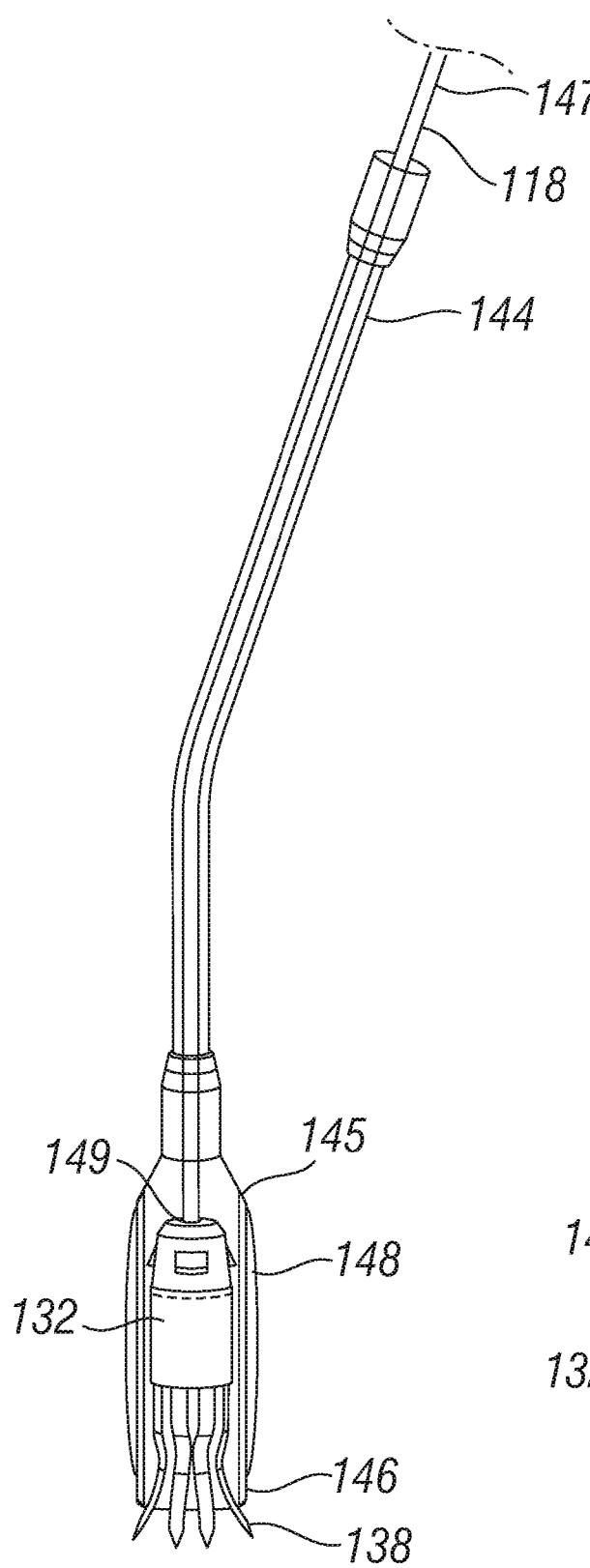
Figure 10D:
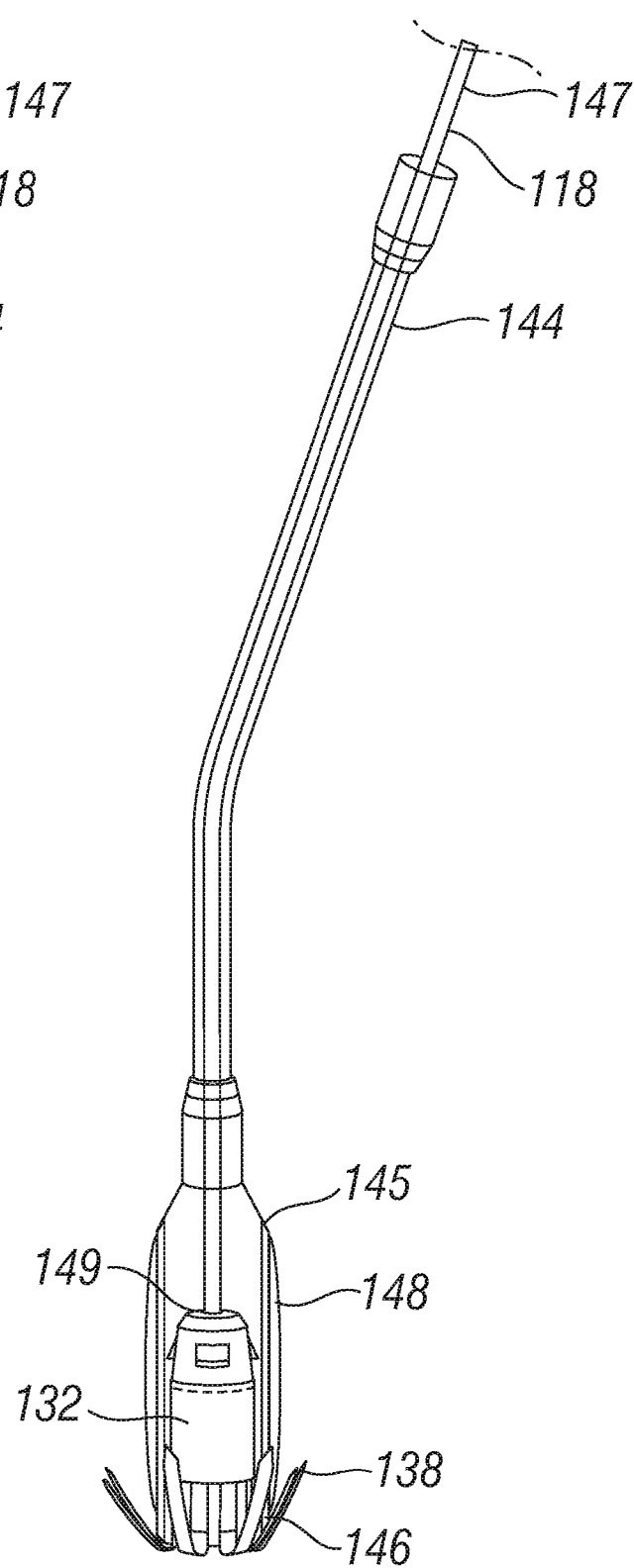

When the anchor delivery catheter distal end portion 145 is advanced such that the anchor portion 132 is properly positioned at a desired target location within the heart, the distal end sheath 146 is retracted proximally with respect to the anchor portion 132, as illustrated in FIGS. 10C and 10D. As the anchor portion 132 is exposed, the prongs 138 expand outwardly. In some embodiments, the expansion of the prongs 138 may advantageously pull the anchor portion 132 out of the anchor delivery catheter 144 and outer sheath 148.

After being released from the outer sheath 148, the prongs 138 on the anchor portion 132 may continue to expand, bending back around towards the generally tubular body 133 while grabbing nearby heart tissue. This tissue-engaging action by the prongs 138 can help to maintain the anchor portion 132 in a stable position within the heart that resists movement due to heart beats, blood flow, and similar actions. In this respect, the anchor portion 132 may at least partially "self-deploy" within the heart, requiring little or no extra pressure from the anchor delivery catheter 144 to anchor within the muscular wall of the heart. Note that although FIGS. 10C and 10D depict the expandable balloon 148 in a deflated condition, the expandable balloon 148 can be left inflated during deployment of the anchor portion 132.

In the embodiments of FIGS. 10A-10D, the anchor line 118 took the form of a wire 147 secured to the anchor portion 132 via an anchor portion connection in the form of a screw-like connection 149, details of which are depicted in greater detail in FIG. 12B. The wire 147 can be relatively thick and configured to transmit axially rotational movement along its length. When the user desires to remove the wire 147, the user can rotate a proximal portion of the wire 147 (which may be positioned outside of the patient's body), thereby causing a corresponding rotation of the distal portion of the wire 147 and the screw-like connection 149 to the anchor portion 132. This rotation will essentially unscrew the screw-like connection 149, thereby disconnecting the wire 147 from the anchor portion 132. The wire 147 can also serve to retract the anchor portion 132 back into the distal end sheath 146 during or after deployment thereof. For example, in the event that the user is not satisfied with the initial deployment of the anchor portion 132, the user can pull on the wire 147 while holding still or even advancing the distal end sheath 146. As the anchor portion 132 is drawn back into the distal end sheath 146, inward pressure on the prongs 138 from the distal end sheath 146 will cause the prongs 138 of the anchor portion 132 to collapse inwardly, thereby collapsing the anchor portion 132 back to its delivery (i.e., predeployment) condition as the anchor portion 132 is pulled back into the distal end sheath 146. The user can then redeploy the anchor portion 132 in a new position, or can remove the anchor portion 132 entirely from the patient.

Figure 11:
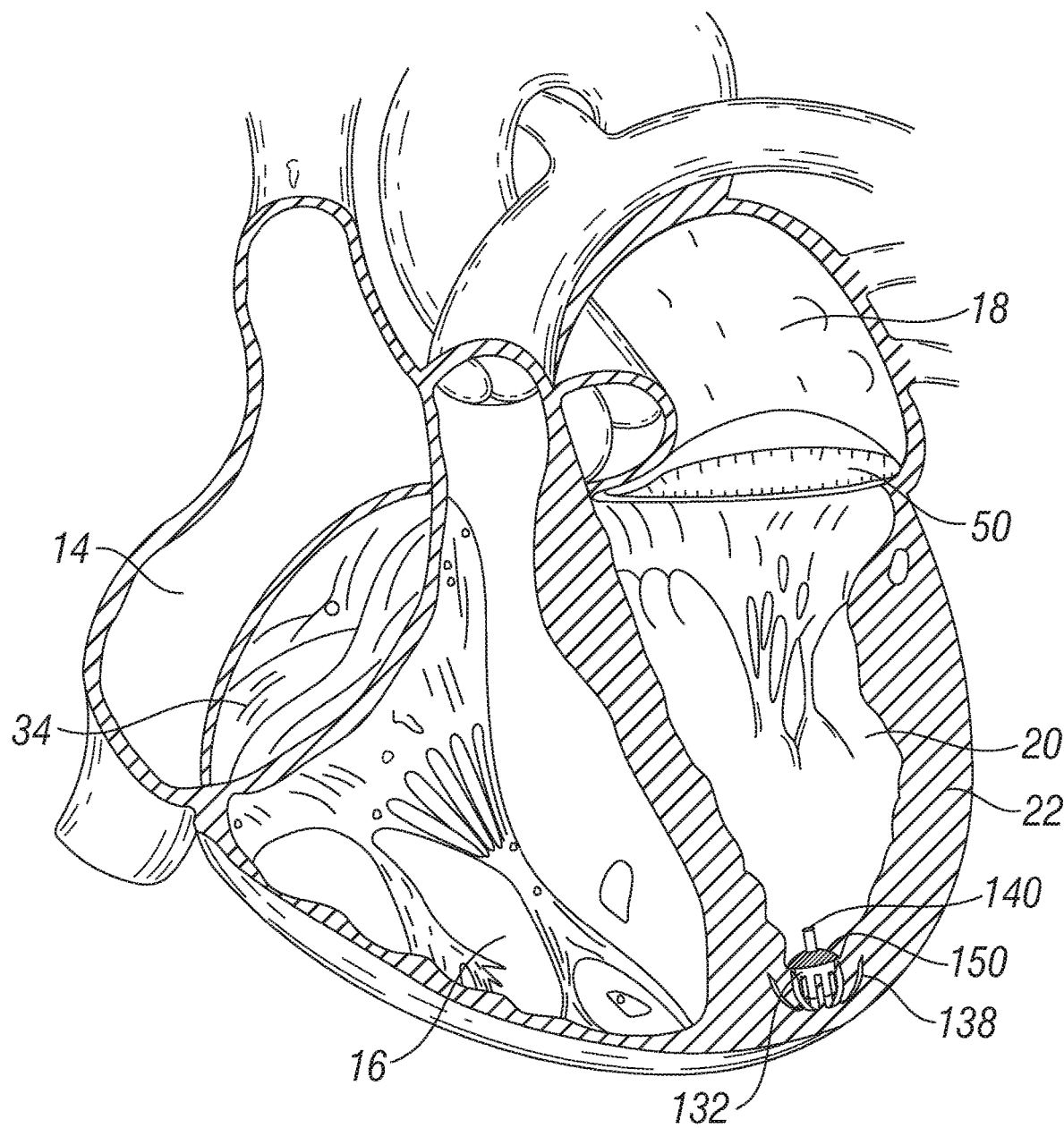
FIG. 11 depicts a front view of a heart, in cross section, with an anchor portion, such as the one depicted in FIGS. 9A and 9B, anchored within a left ventricle muscle.

With reference now to FIG. 11, the anchor portion 132 is shown some time after anchor deployment into the muscular wall of the left ventricle 20 (i.e., after the first stage of the implantation procedure). After implantation in the heart 12, endocardial tissue 150 has grown over the exposed tubular portion 133 of the anchor portion 132 that is protruding from the muscular wall 22 into the left ventricle 20, preferably leaving only the anchor coupling member 140 exposed within the left ventricle 20. Simultaneously, inside the heart wall 22 around the embedded portions of the anchor portion 132 a scarring healing takes place, wherein fibrocytes create strong scarring tissue surrounding the prongs 138, thereby integrating them with the muscle of the heart wall 22 to create a very strong attachment. It has been found that adequate tissue overgrowth on the exposed areas of the anchor portion 132 and the scar healing around the prongs 138 may occur in two or three weeks. However, the amount of time required may depend on various factors, such as the location of the anchor portion 132 within the heart 12, the surface features or coatings of the anchor portion 132, and finally the health status and other characteristics of the patient.

The coupling member 140 provides a point of attachment for connecting a valve portion (such as the elongate body portion 74, tethers 78, and canopies 76 of previously described preferred embodiments) during a second or later implantation stage. During the second stage, the valve portion may be delivered into the heart using a procedure similar to that described above with respect to FIGS. 8A-8E.

Note that FIG. 11 does not depict an anchor line (such as the anchor line 118 in the form of the wire 147 from FIGS. 10A-10D) as being present, although depending on the particular embodiment and application one or more anchor lines may be left attached to the anchor after anchor deployment for subsequent use in guiding the expandable valve portion to the anchor during attachment of the expandable valve portion to the anchor. While a user may be able to couple the valve portion to the anchor portion by simply searching around the patient's heart, additional techniques can be used to facilitate this procedure. For example, anchor lines such as those depicted and described with respect to FIGS. 8A-8E and FIGS. 10A-10D could be used, such as where an anchor line is left secured to the coupling member during the first implantation stage and left within the patient for use during the second stage. During the second implantation stage, the attachment mechanism of the valve portion can attach to the thread, which guides the attachment mechanism directly to the coupling member located on the anchor portion within the heart. As another example, both the coupling member on the anchor portion and the corresponding attachment mechanism of the valve portion may be magnetized, thereby allowing the two to be drawn together when in close proximity. In yet another example, navigation can be facilitated with cameras, X-rays, or similar techniques which allow the user to visualize the coupling member within the patient. In still another example, a vacuum assisted connection is used to facilitate connection of the valve portion to the coupling member.

FIGS. 12A-12B depict a further embodiment of connection mechanisms applicable to an anchor 132 and elongate body portion 152. In the particular embodiment depicted, the anchor proximal end 136 includes a coupling member 140 in the form of a generally tubular projection 154 having outwardly extending locking clips 156 that can be bent inwardly in response to inward pressure but will snap back outward once the inward pressure is released. The elongate body portion 152 has a distal end 158 including an attachment mechanism 160 with a ring-like structure 162 configured to be advanced along the anchor line 118 and to pass generally tightly around the anchor generally tubular projection 154.

The anchor portion 132 includes an anchor line connection in the form of an inner lumen 151 configured to receive and interactively couple with the screw-like anchor connection 149 of the wire 147 of the anchor line 118. The interaction between the anchor portion inner lumen 151 and screw-like anchor connection 149 thus secures the anchor line 118 to the anchor portion 132.

The ring-like structure 162 can be advanced to the anchor portion 132 along the anchor line 118, with the wire 147 of the anchor line 118 serving as a guide to lead the ring-like structure 162 to the generally tubular projection 154 of the anchor portion 132. As the ring-like structure 162 passes over the generally tubular projection 154 of the anchor portion 132, the locking clips 156 are forced inward by pressure from the ring-like structure 162, but then spring back outwardly to lock onto an inner ridge 164 inside the ring-like structure 162, thereby locking the elongate body portion 152 to the anchor portion 132 as depicted in FIG. 12B.

After the elongate body portion 152 is secured to the anchor portion 132, the anchor line 118 can be disconnected from the anchor portion 132 by rotating the wire 147 to "unscrew" the screw-like anchor connection 149 of the wire 147 from the anchor portion inner lumen 151. With the anchor line 118 disconnected from the anchor 132, the anchor line 118 can be removed from the patient.

Figures 13A, 13B:
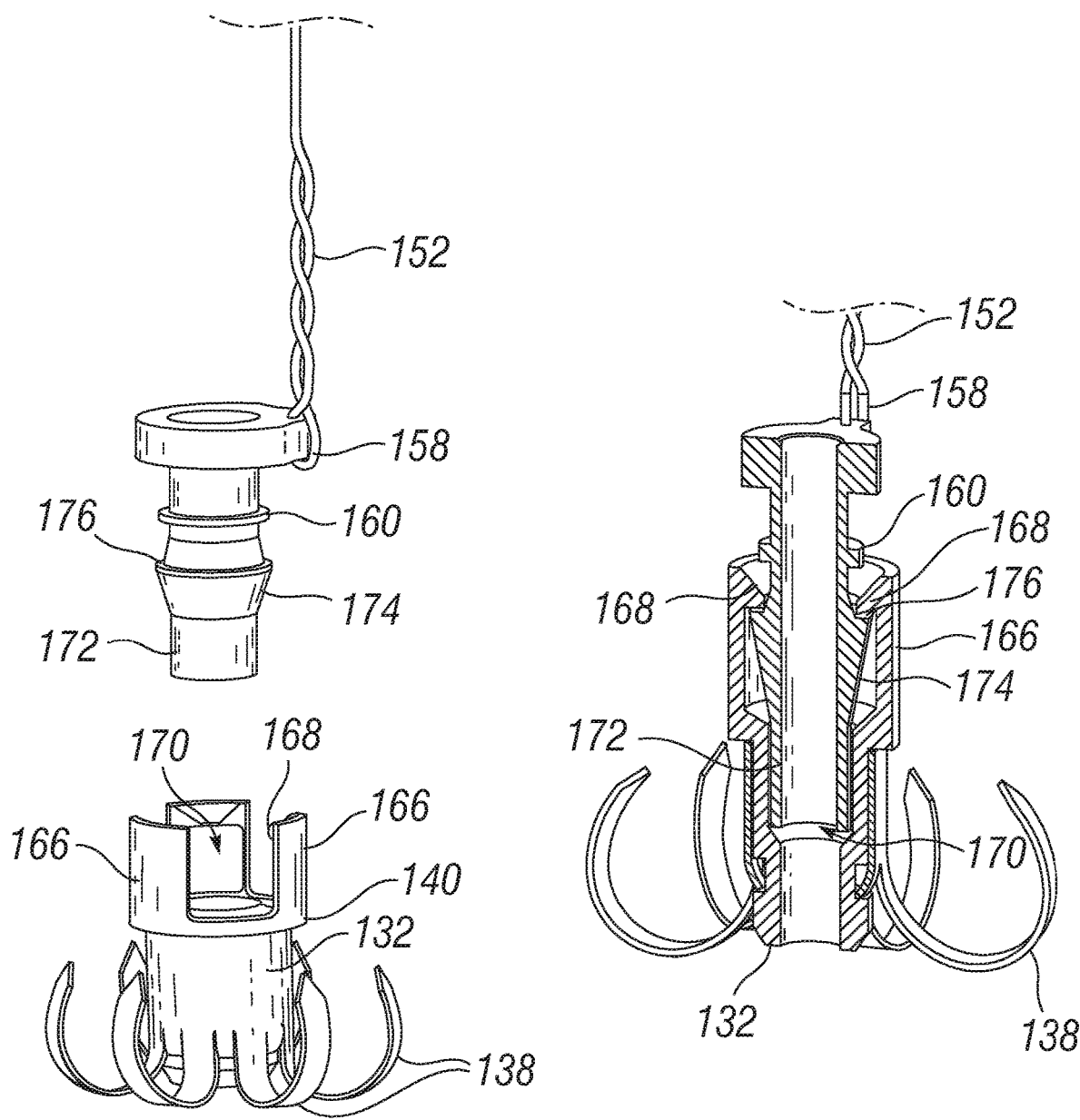
FIG. 13A depicts a perspective view of an anchor portion and elongate body portion with connectors according to an embodiment of the invention prior to attachment.
FIG. 13B depicts a perspective view, in cross section, of the anchor portion and elongate body portion with connectors from FIG. 13A in an attached condition.

FIGS. 13A-13B depict a further embodiment of connection mechanisms applicable to an anchor 132 and elongate body portion 152. In the particular embodiment depicted, the anchor proximal end 136 includes a coupling member 140 in the form of a plurality of locking extensions 166 having inwardly-directed projections 168, with the locking extensions 166 forming a generally tubular (albeit radially incomplete) structure defining an anchor lock opening 170 therein. The locking extensions 166 can be bent outwardly in response to outward pressure, but will snap back inward once the outward pressure is released. The elongate body portion 152 has a distal end 158 including an attachment mechanism 160 with a generally tubular structure 172 configured to pass generally tightly into the anchor lock opening 170. The generally tubular structure 172 includes a generally conical surface 174 angled to gently ease the anchor locking extensions 166 outwardly as the generally tubular structure is advanced into the anchor lock opening 170. The generally conical surface 174 ends in a disk-like surface 176 configured to interact with the inwardly-directed projections 168 of the anchor locking extensions 166 to prevent the attachment mechanism 160 from being removed from the coupling member 140, as depicted in FIG. 13B.

Figure 14:
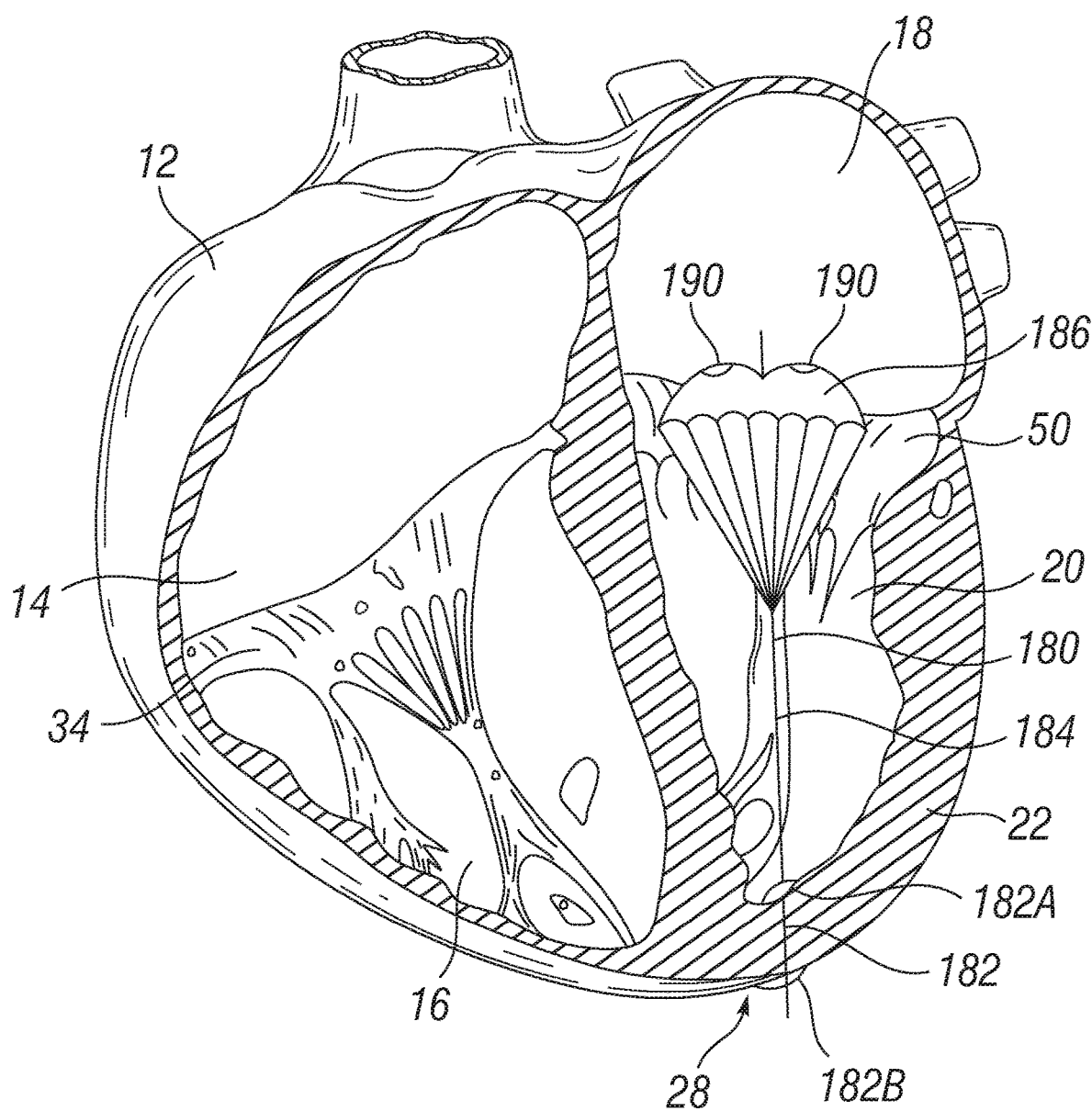
FIG. 14 depicts a front view of a heart, in cross section, with a device according to an embodiment of the invention.

With reference now to FIG. 14, an alternative blood flow controlling device 180 includes an anchor portion 182 configured for penetrating the heart wall 22 within the left ventricle 20. In the illustrated embodiment, the anchor portion 182 includes an inner anchor plate 182b and an outer anchor plate 182b. In preferred embodiments, the inner and outer plates 182a, 182b may be made of a shape-memory material, such as, for example, Nitinol. As a result, the plates 182a, 182b may be constrained in a collapsed configuration during delivery and then self-expand when ejected from a delivery catheter. In the expanded configuration, the plates 182a and 182b prevent the generally elongate body 184 of the device 180 from moving relative to the heart wall 22. Over time, the anchor portion 182 becomes overgrown with tissue which further secures the device 180 within the heart 12. The canopy 186 or other blocking structure secured to the elongate body portion 184 serves to at least partially block the mitral valve opening to prevent mitral valve regurgitation.

Although a variety of anchor embodiments have been described for purposes of illustration, it will be appreciated that a wide variety of anchor devices may be utilized while remaining within the scope of the invention. For example, anchor members such as hooks, arms, sutures or other suitable structures may be used. In other configurations, anchor portions used with the blood flow controlling device may be shaped for attachment to different locations in the heart. Although certain delivery methods have been described above with respect to anchor portions shaped for attachment to the ventricular wall, anchor portions may be shaped for deployment within a left or right atrium.

With further reference to FIG. 14, the device 180 includes apertures 190 in the canopy 186 that may reduce the formation of clots, thrombosis, embolism, and similar complications that might be caused by stagnant blood that might become trapped within the curvature of the canopy 186. The apertures 190 allow a small amount of blood to pass through the canopy 186 when the valve 50 and the device 180 are in a closed position, allowing movement and circulation of the blood near the canopy 186.

In the embodiment depicted in FIG. 14, two apertures 190 are shown in the canopy 186; however, other numbers and arrangements of the apertures 190 are also within the scope of the invention. For example, a single aperture may be located near the center of a canopy or other blood-flow blocking structure. In another example, a plurality of small apertures can be distributed across a canopy or other blood-flow blocking structure.

In many of the above figures, the blood flow controlling device includes a generally parachute-like structure that acts to at least partially block the valve opening. However, other structures for at least partially blocking the valve opening are also within the scope of the invention, including hinged structures, solid structures, etc.

The desired distance from an anchor portion to the canopy or other blood-flow blocking device depends on various factors, such as the desired anchor deployment location, the size of the heart, the condition of the heart valve, etc. The specific distance for a particular patient or procedure may not be evident until the procedure is actually underway. It may thus be desirable to have a device in which the distance between the anchor and blood-flow blocking device can be easily adjusted by the surgeon or other user.

Figures 15, 16:
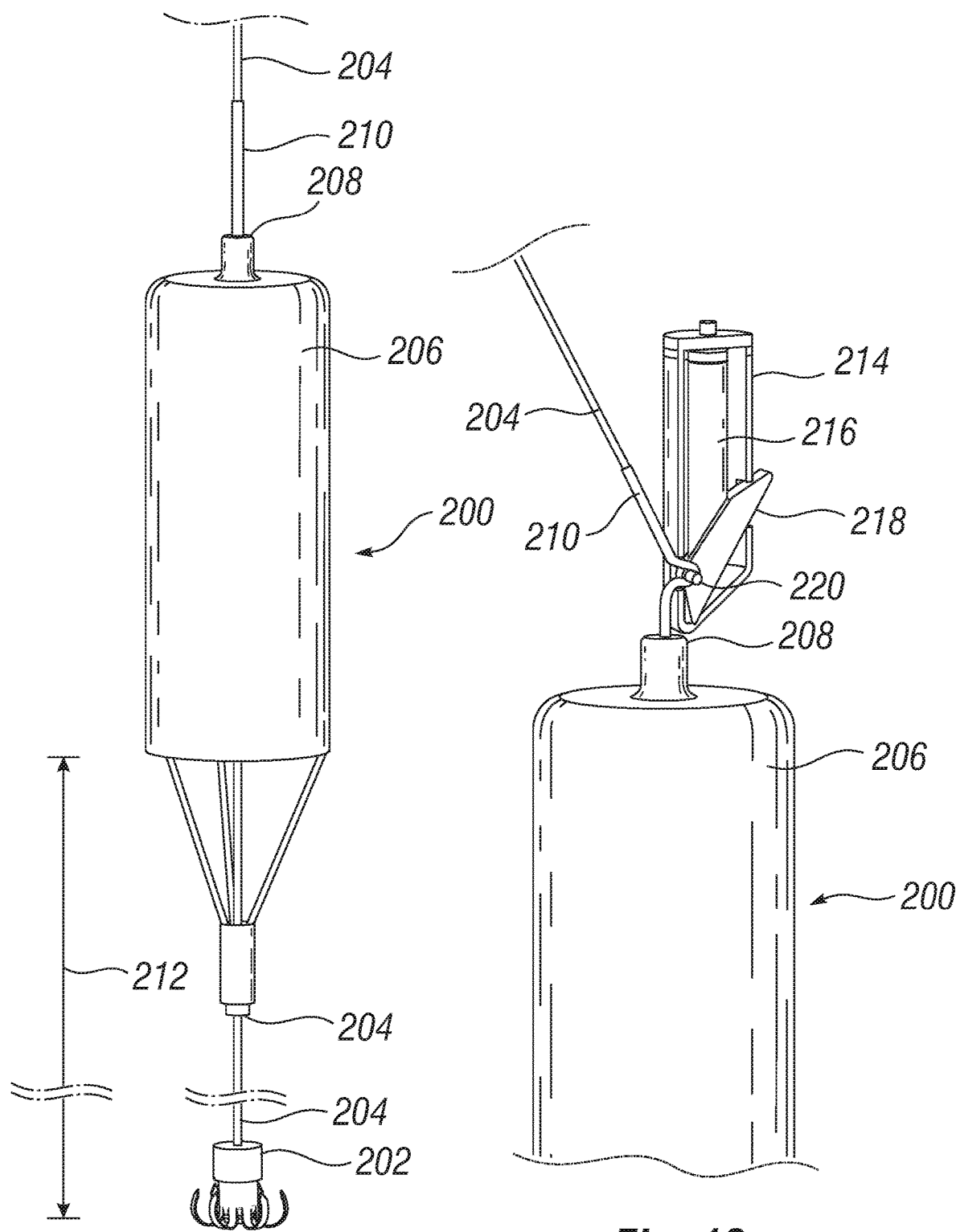
FIGS. 15 and 16 depict side views (with 16 being a close-up view) of a device according to an embodiment of the invention.

FIGS. 15 and 16 depict a device 200 that includes an anchor portion 202, an elongate body portion 204, and a blood-flow blocking portion 206. The blood-flow blocking portion 206 is positioned on the elongate body portion 204, with the elongate body portion 204 slidingly passing inside of the blood-flow blocking portion 204 and exiting from its top 208 through a bendable lumen 210. The bendable lumen 210 is plastically deformable. The user can slide the blood-flow blocking portion 204 up and down with respect to the anchor portion 202. When the distance 212 between the blood-flow blocking portion 206 and the anchor portion 202 is determined to be optimal (which the surgeon or other user can determine in a beating heart by observing the heart function via various procedures and methods, including fluoroscopy, echo, etc.), the user can lock the blood-flow blocking portion onto the elongate body portion 204 by deforming the bendable lumen 210 to a shape that will no longer permit the elongate body portion 204 to slide therethrough, as depicted in FIG. 16. In the particular embodiment depicted, the deformation of the bendable lumen 210 is achieved by a locking catheter 214 which is slidingly advanced along the elongate body portion 204 and over the bendable lumen 210. When an inner structure 216 of the locking catheter 214 is engaged against an at least partially rotatable wedge-like structure 218, the wedge-like structure 218 pulls on a knob 220 which pulls the bendable lumen 210 into the locking catheter 214 and causes the bendable lumen 210 to deform to a bent shape that no longer permits the elongate body portion from sliding therethrough.

Figure 17:
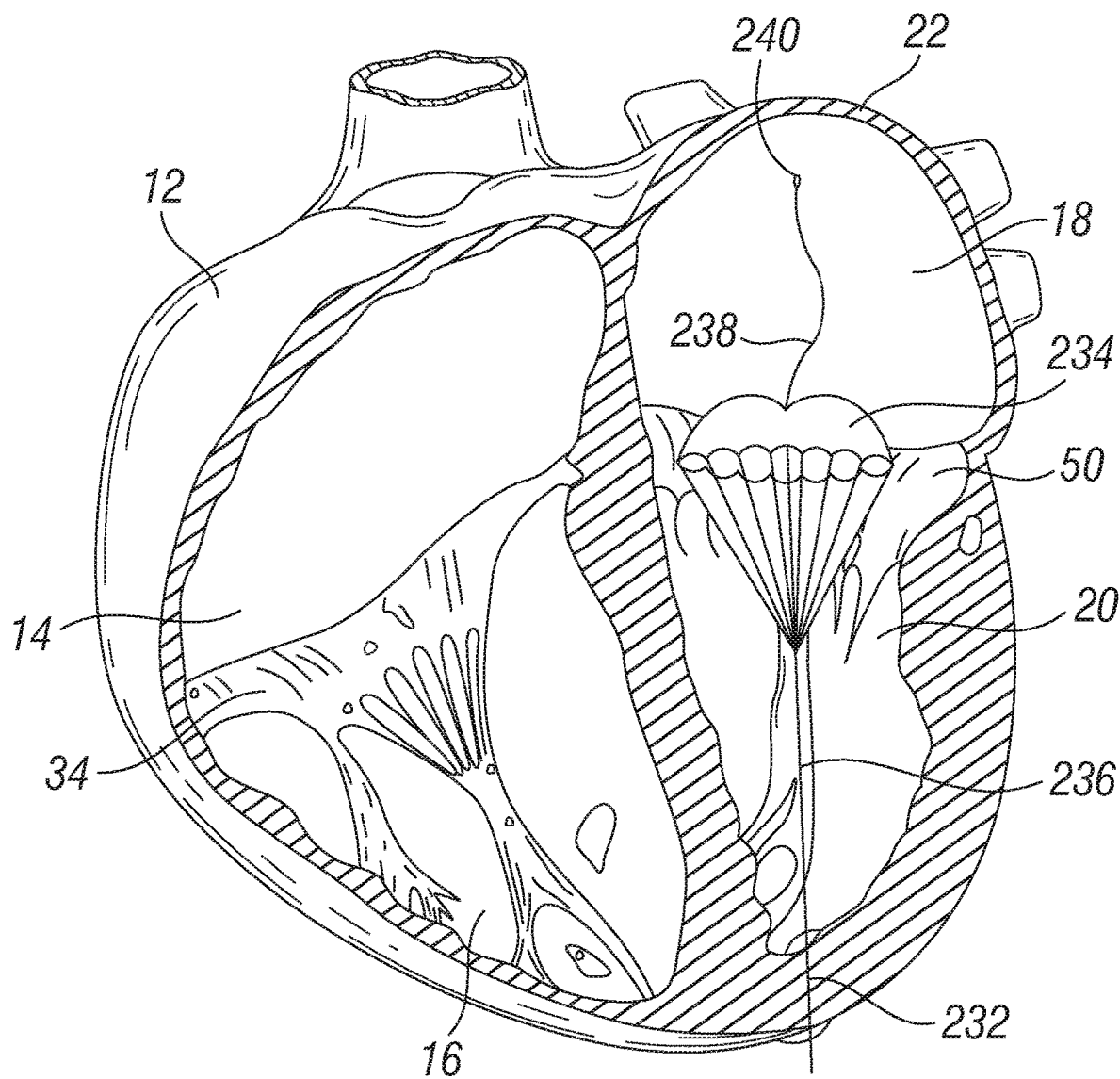
FIG. 17 depicts a front view of a heart, in cross section, with a device according to a further embodiment of the invention.

FIG. 17 depicts a further embodiment of the invention, wherein a device 230 includes an anchor portion 232, a blood-flow blocking portion 234, and a spacer portion 236 in the form of an elongate body configured to permit the blood-flow blocking portion 234 to be positioned at a distance from the anchor portion 232 for placement at or adjacent a valve, which in the particular embodiment is a mitral valve 50. The device 230 further includes a leash 238 which is secured at one end to the blood-flow blocking portion 234 and at the other end to tissue 240 of the heart wall 22 within the left atrium 18. The leash 238 generally restrains unwanted movement of the blood-flow blocking portion 234. For example, the leash 238 may prevent the blood-flow blocking portion 234 from moving out of the desired location at or adjacent the opening in the valve 50. The leash 238 may be relatively loose, so that it only restrains movement of the blood-flow blocking portion 234 it the blood-flow blocking portion 234 moves significantly from the desired location, such as may be the case in the event of a catastrophic failure of the anchor 232 or spacer portion 236. The leash 238 may also be useful for embodiments wherein the spacer portion 236 is generally flexible, such as where the spacer portion 236 is suture, in which case the least 238 will serve to prevent the blood-flow blocking portion 234 from moving toward the anchor portion 232.

Figure 18:
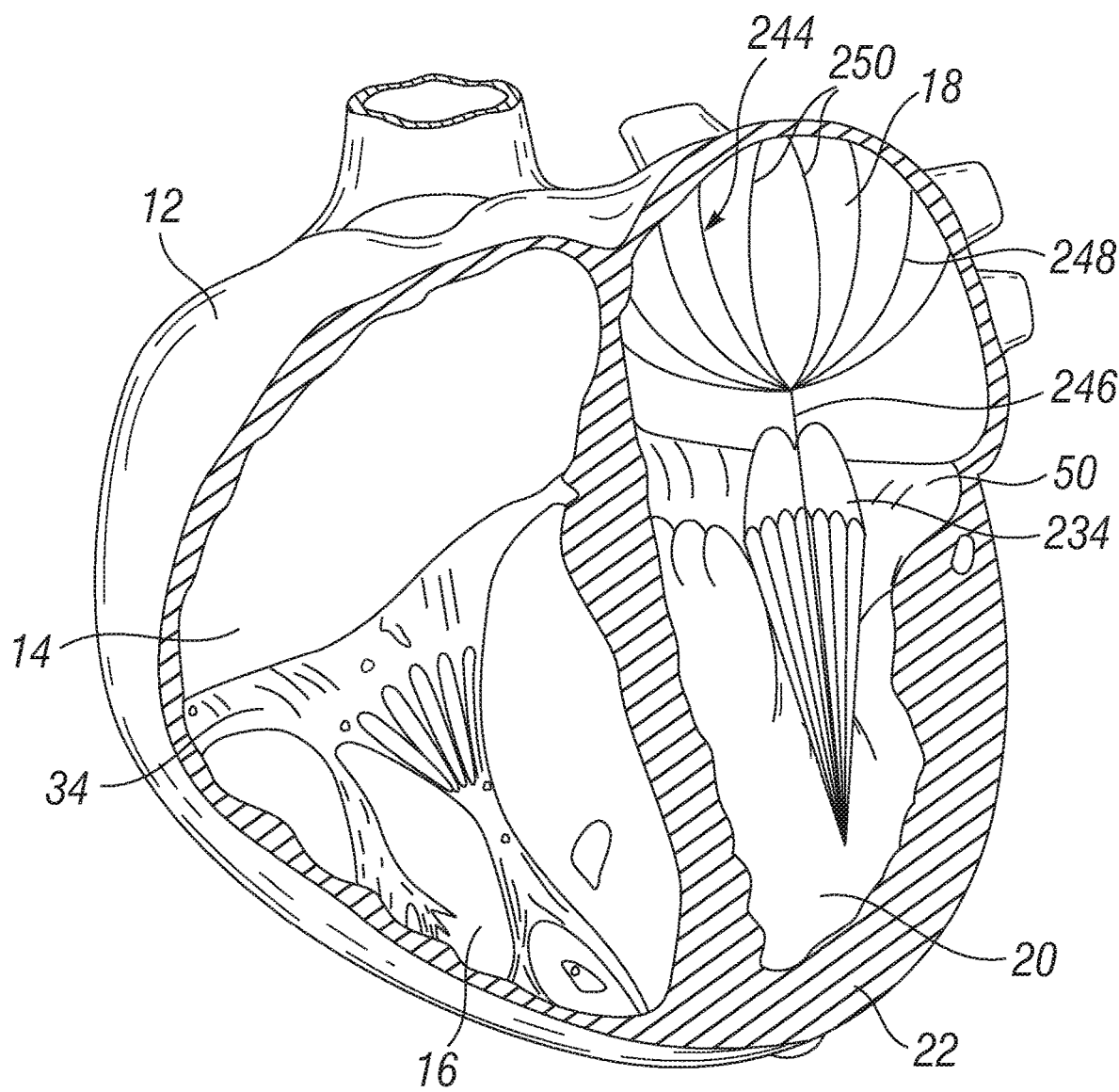
FIG. 18 depicts a front view of a heart, in cross section, with a device according to a further embodiment of the invention.

With some blood flow controlling devices, it may be desirable to construct anchor portions having relatively complicated geometries to better maintain the position of the device within the heart. For example, geometries of anchor portions that more precisely conform to the contours of a heart chamber may be more likely to remain in a desired position and orientation within the heart. Examples of such devices are disclosed in pending U.S. Utility patent application Ser. No. 11/227,642, entitled "Device and Method for Treatment of Heart Valve Regurgitation," which was filed on Sep. 24, 2005, now Pub. No. 2006/0058871, the entire contents of which are expressly incorporated herein by reference. FIG. 18 depicts a device 240 including a blood-flow blocking portion (i.e., valve portion) 242 and an anchor portion 244. A relatively short space portion 246 may also be included. The particular anchor portion 244 is a generally cage-like structure 248 formed generally in the shape of the left atrium 18 and configured for deployment therewithin. A plurality of wire-like elements 250 forms the cage-like structure 248. The wire-like elements 250 may be formed from a shape-memory material, such as Nitinol, with the general shape of the right atrium "programmed" into the shape-memory material of cage-like structure during its construction using known techniques, such as heat treatment. The anchor portion 244 can thus be compressed for delivery into the right atrium 18, and then expanded in situ wherein the body temperature of the patient will cause the cage-like structure 248 to assume its programmed shape to correspond to the shape of the right atrium 18.

Complex shapes such as shapes corresponding to a particular heart chamber of a particular patient can be difficult and time consuming with commonly used metal jigs. Another embodiment of the present invention is directed to devices and methods configured for facilitating the construction of anchor portions, such as the anchor portion 244 from FIG. 18, having complex geometries. In one preferred embodiment, a disposable jig is provided on which an anchor portion may be shaped to conform to the anatomy of the target location. Initially, a master jig shape is created from which disposable jigs are later created. The shape of the jigs provides the surfaces on which the shape memory material (e.g., Nitinol) is shaped. Preferably, this master jig can be designed with 3D CAD software, and then created using 3D stereolithography printers, such as those from Z Corp. of Burlington, Mass. Alternately, the master jig can be created by hand.

With reference to FIGS. 19A and 19B, in one preferred embodiment, a master jig 300 is created from a 3D CAD design and a 3D printer. The master jig 300 includes a plurality of channels 302 and 303 into which shape-memory wire or retaining members can later be placed on the disposable copy of the jig 300. Since the master jig 300 of the present example is created with a 3D printer which "prints" with a plastic, the master jig 300 includes an expansion hole 304 to prevent the shape of the master jig 300 from distorting as it cools.

Next, a mold 306 is created from the master jig 300 from which disposable jigs are later created, as depicted in FIG. 20. The mold 306 can be created by placing the master jig 300 into a container and filing the container with liquid silicone. The silicone is allowed to solidify and is then cut in half to remove the master jig 300. This leaves an impression of the master jig 300 in the silicone which becomes the disposable jig mold 306.

Each disposable jig is formed from a liquid material that hardens within the mold 306. Since the shape memory materials that are later placed on the disposable jigs are typically heat treated to retain their jig shape, the disposable jig material is preferably heat resistant also. One example of a disposable jig material is commonly known as dental gypsum (e.g., semi-hydrate calcium sulphate) which is commonly used in the dental community for making molds and impressions of teeth. Dental gypsum is poured into each half of the mold 306 (which has been previously split open to remove the master jig 300). The dental gypsum is typically mixed into a liquid/paste form and allowed to harden to the shape of the mold 306 (hardening typically takes about 3 hours). The end result of filing the mold 306 is a solid jig, including the shape and depressions of the original master jig 300.

Figure 21:
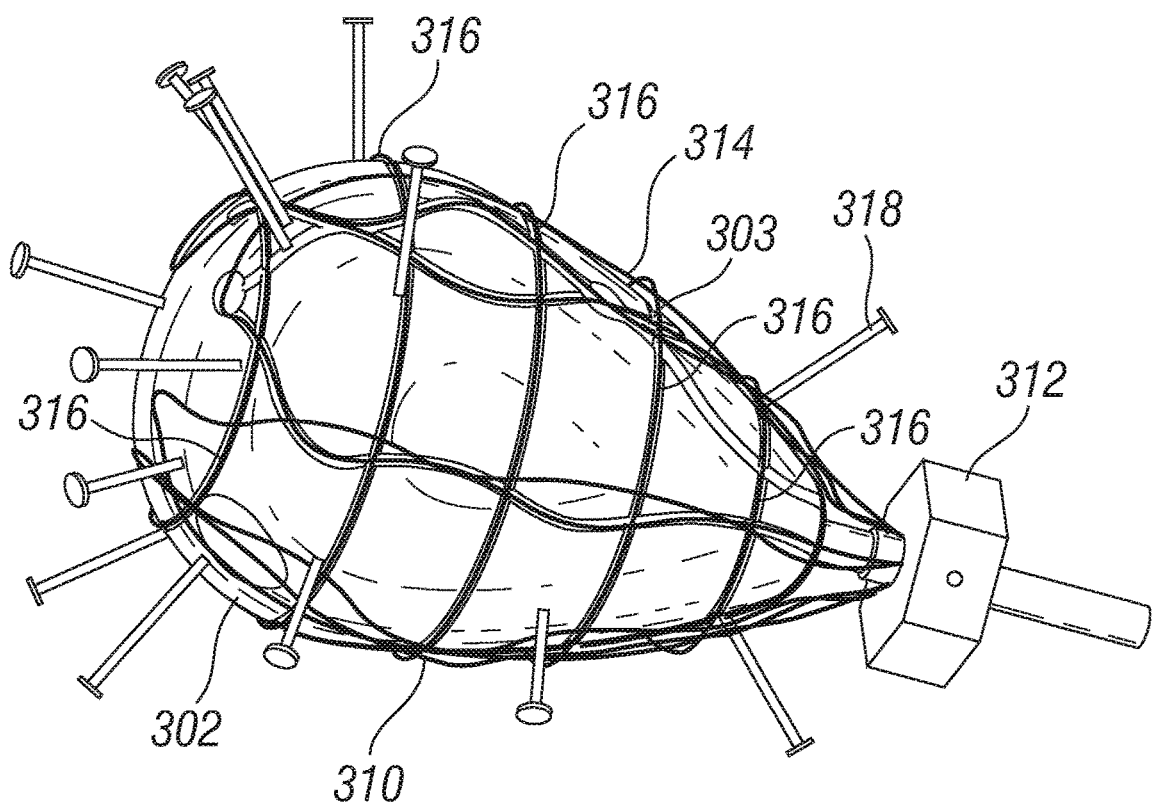
FIG. 21 is a perspective view of a disposable jig formed using the silicone model of FIG. 20.

With reference to FIG. 21, a disposable jig 310 is formed from the previously described mold 306. As shown in the illustrated embodiment, shape memory wires 314 are positioned within the longitudinal channels 302 along the jig 310. Prior to heat treatment to change the relaxed shape of the shape-memory wire 314, the shape-memory wire 314 may not maintain its position within the channels 302. Thus, retaining elements such as circular wires 316 and pins 318 may be used to hold the shape-memory wire 314 in place. In the present example, the circular wires 316 are placed within latitudinal channels 303, crossing over the shape-memory wires 314. Similarly, pins 318 are positioned at various locations near the wires 314 and 316 to maintain the wire's position on the jig 310.

The disposable jig 310 may also include a mounting bracket 312 which locks onto the free ends of the shape-metal wires 316. The mounting bracket 312 also provides a mounting point by which the jig 310 can be mounted onto a vice or other tool.

Figure 22:
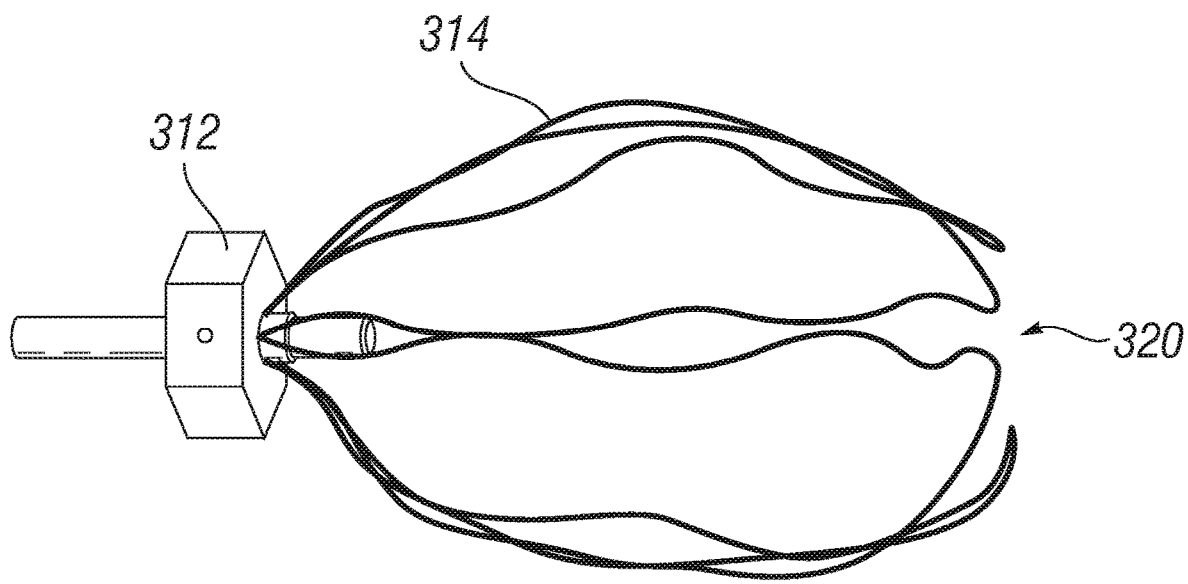
FIG. 22 is a perspective view of an anchor device formed from the disposable jig of FIG. 21.

When the shape-memory wires 316 have been secured on the jig 310 at a desired location, the jig 310 is placed into a heat source, such as an oven. This heat sets the shape of the shape-memory metal 314 as is well known in the art. After the heat, the user is free to remove the shape-memory wires 314 from the jig 310. Since the jig 310 is disposable and preferably made from dental gypsum, the user may wish to break the jig 310 with a hammer to quickly remove the newly formed anchoring region 320, as seen in FIG. 22.

In one example of such a heating process, a 50 gram gypsum jig 310 with Super Elastic Alloy N Nitinol wires 314 can be heated to about 570 degrees Celsius for about 20 minutes. The jig 310 is then removed to air cool for less than a minute and then rapidly cooled in room temperature water. The wires 314 can be removed from the jig (e.g., the jig can be broken), placed back into the heat source for about 10 minutes, then cooled in the same manner as previously described.

The invention has generally been described herein for use in minimally-invasive procedures conducted through one or more relatively small incisions in the chest cavity. However, the devices and methods of the invention could also be applicable in other procedures, such as in general (e.g., open-chest) surgical procedures and percutaneous procedures.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A method of deploying a blood-flow controlling device for treating a mitral or tricuspid valve in need thereof, the method comprising:
    providing a blood-flow controlling device having:
        a blood-flow blocking portion slidable over a flexible, elongate body portion, the blood-flow blocking portion comprising an elongate structure with a substantially cylindrical portion, a portion of the blood-flow blocking portion configured to be disposed between leaflets of a native mitral or tricuspid valve and the blood-flow blocking portion being fillable with blood, and
        an anchor disposed on a distal end of the elongate body portion, the anchor engageable with heart tissue at or adjacent a heart apex, the anchor comprising a tubular body and a plurality of pointed, elongated prongs emanating from a distal end of the tubular body, the plurality of elongated prongs self-expandable from a compressed configuration, in which the plurality of elongated prongs extend distally, and an expanded configuration, in which the plurality of elongated prongs are deflected radially outward relative to a center of the tubular body;
    providing an anchor delivery catheter for delivering the anchor having a distal end sheath that maintains the plurality of elongated prongs in the compressed configuration;
    advancing the anchor delivery catheter through the mitral or tricuspid valve and into an adjacent ventricle;
    deploying the anchor in ventricular tissue by expelling the anchor from the distal end sheath;
    sliding the blood-flow blocking portion relative to the elongate body portion and positioning the blood-flow blocking portion between the leaflets of the mitral or tricuspid valve;
    providing a locking catheter slidable along the elongate body portion,
    locking the blood-flow blocking portion to the elongate body portion with the locking catheter, preventing sliding therebetween.

2. The method of claim 1, wherein the blood-flow blocking portion further comprises a bendable lumen through which the elongate body portion extends, the method including using the locking catheter to deform the bendable lumen and lock the blood-flow blocking portion to the elongate body portion.

3. The method of claim 2, wherein the bendable lumen is within a bendable tube extending from a proximal end of the blood-flow blocking portion, the bendable tube being plastically deformable to lock the blood-flow blocking portion to the elongate body portion.

4. The method of claim 1, wherein the anchor delivery catheter includes an expandable balloon positioned around a portion of the distal end sheath, the expandable balloon being expandable during the step of advancing the anchor delivery catheter so as to assist in advancement thereof by preventing entanglement of the anchor with chordae tendinae and other sub-valvular structures.

5. The method of claim 1, wherein the anchor further comprises a coupling member to which a connector at the distal end of the elongate body portion is couplable.

6. The method of claim 1, further including a leash extending from a proximal end of the blood-flow blocking portion, the method including anchoring the leash to tissue in an atrium adjacent the mitral or tricuspid valve and restrain unwanted movement of the blood-flow blocking portion.

7. The method of claim 1, wherein the blood-flow blocking portion is dimensioned for positioning between leaflets of the native mitral valve.

8. The method of claim 1, wherein the blood-flow blocking portion is dimensioned for positioning between leaflets of the native tricuspid valve.

9. A method of deploying a blood-flow controlling device for treating a mitral or tricuspid valve in need thereof, the method comprising:
    providing a blood-flow controlling device having:
        a blood-flow blocking portion slidable over a flexible, elongate body portion, the blood-flow blocking portion comprising an elongate structure, a portion of the blood-flow blocking portion disposable between leaflets of a native mitral or tricuspid valve and Tillable with blood, and
        an anchor disposed on a distal end of the elongate body portion, the anchor engageable with heart tissue at or adjacent a heart apex;
    providing an anchor delivery catheter for delivering the anchor having a distal end sheath from which the anchor is expelled;

advancing the anchor delivery catheter through the mitral or tricuspid valve and into an adjacent ventricle;

deploying the anchor in ventricular tissue;

sliding the blood-flow blocking portion relative to the elongate body portion and positioning the blood-flow blocking portion between the leaflets of the mitral or tricuspid valve;

providing a locking catheter slidable along the elongate body portion, locking the blood-flow blocking portion to the elongate body portion with the locking catheter, preventing sliding therebetween.

10. The method of claim 9, wherein the blood-flow blocking portion comprises a substantially cylindrical portion.

11. The method of claim 9, wherein the anchor comprises an inner anchor plate and an outer anchor plate.

12. The method of claim 9, wherein the anchor comprises a tubular body and a plurality of pointed, elongated prongs emanating from a distal end of the tubular body, the plurality of elongated prongs self-expandable from a compressed configuration, in which the plurality of elongated prongs extend distally, and an expanded configuration, in which the plurality of elongated prongs are deflected radially outward relative to a center of the tubular body.

13. The method of claim 9, wherein the anchor further comprises a coupling member to which a connector at the distal end of the elongate body portion is couplable.

14. The method of claim 9, wherein the blood-flow blocking portion further comprises a bendable lumen through which the elongate body portion extends, the method including using the locking catheter to deform the bendable lumen and lock the blood-flow blocking portion to the elongate body portion.

15. The method of claim 14, wherein the bendable lumen is within a bendable tube extending from a proximal end of the blood-flow blocking portion, the bendable tube being plastically deformable to lock the blood-flow blocking portion to the elongate body portion.

16. The method of claim 9, wherein the blood-flow blocking portion is dimensioned for positioning between leaflets of the native mitral valve.

17. The method of claim 9, wherein the blood-flow blocking portion is dimensioned for positioning between leaflets of the native tricuspid valve.

18. The method of claim 9, wherein the anchor comprises a plurality of elongated prongs self-expandable from a compressed configuration, and the anchor delivery catheter distal end sheath maintains the plurality of elongated prongs in the compressed configuration, and the step of deploying the anchor in ventricular tissue includes expelling the anchor from the distal end sheath.

19. The method of claim 18, wherein the anchor delivery catheter includes an expandable balloon positioned around a portion of the distal end sheath, the expandable balloon being expandable during the step of advancing the anchor delivery catheter so as to assist in advancement thereof by preventing entanglement of the anchor with chordae tendinae and other sub-valvular structures.

20. The method of claim 9, further including a leash extending from a proximal end of the blood-flow blocking portion, the method including anchoring the leash to tissue in an atrium adjacent the mitral or tricuspid valve and restrain unwanted movement of the blood-flow blocking portion.

* * * * *